United States Patent
Ball et al.

(10) Patent No.: US 11,071,853 B2
(45) Date of Patent: Jul. 27, 2021

(54) SYSTEM AND METHOD FOR STERILIZATION USING ULTRAVIOLET RADIATION

(71) Applicant: UV Light Care, Inc., Boston, MA (US)

(72) Inventors: Anthony Ball, Mendon, MA (US);
Adam Push, Boston, MA (US);
Abraham Seckler, Boston, MA (US)

(73) Assignee: UV Light Care, Inc., Boston, MA (US)

( * ) Notice: Subject to any disclaimer, the term of this patent is extended or adjusted under 35 U.S.C. 154(b) by 0 days.

(21) Appl. No.: 15/628,792

(22) Filed: Jun. 21, 2017

(65) Prior Publication Data

US 2018/0369560 A1    Dec. 27, 2018

(51) Int. Cl.
*A61M 39/16* (2006.01)
*F21V 8/00* (2006.01)
(Continued)

(52) U.S. Cl.
CPC ............... *A61M 39/16* (2013.01); *A61L 2/10* (2013.01); *A61M 39/10* (2013.01);
(Continued)

(58) Field of Classification Search
None
See application file for complete search history.

(56) References Cited

U.S. PATENT DOCUMENTS

| 4,266,815 A | * | 5/1981 | Cross | F16L 37/244 |
| | | | | 285/330 |
| 4,816,145 A | * | 3/1989 | Goudy, Jr. | A61L 2/10 |
| | | | | 210/243 |

(Continued)

FOREIGN PATENT DOCUMENTS

| EP | 2161040 A1 | 3/2010 | |
| JP | 08266595 A | * 10/1996 | ............... A61L 2/10 |

(Continued)

OTHER PUBLICATIONS

Sun, et al., "Analysis of the Far-Field Region of LEDS", "Optics Express", Aug. 3, 2009, pp. 13918-13927, vol. 17, No. 16, Published in: USA.

(Continued)

*Primary Examiner* — Michael J Logie
(74) *Attorney, Agent, or Firm* — Loginov & Associates. PLLC; William A. Loginov

(57) ABSTRACT

This invention provides a system and method for sterilizing an ISO 594 female Luer fitting and an attached catheter using UV light. An optical plug can be inserted into a female Luer fitting, and UV-C light or a combination of UV-C and UV-A light can be radiated through the optical plug and into the female Luer fitting and attached catheter, thereby sterilizing the fitting and catheter. A sterilizer device can be used to hold the female Luer fitting and catheter, with an optical plug inserted into the female Luer fitting. The sterilizer device can include a UV light source that radiates UV light through the optical plug and into the female Luer fitting and attached catheter. A protective cover can be placed over the optical plug before inserting the optical plug into the female Luer fitting. The protective cover can be disposable.

17 Claims, 22 Drawing Sheets

(51) Int. Cl.
*A61M 39/10* (2006.01)
*A61L 2/10* (2006.01)

(52) U.S. Cl.
CPC ........ *G02B 6/0096* (2013.01); *A61L 2202/24* (2013.01); *A61M 2039/167* (2013.01)

(56) References Cited

U.S. PATENT DOCUMENTS

| | | | |
|---|---|---|---|
| 5,637,877 A * | 6/1997 | Sinofsky | A61L 2/10 250/492.1 |
| 6,403,030 B1 | 6/2002 | Horton, III | |
| 6,447,720 B1 | 9/2002 | Horton et al. | |
| 6,447,721 B1 | 9/2002 | Horton, III et al. | |
| 6,454,937 B1 | 9/2002 | Horton et al. | |
| 6,461,569 B1 * | 10/2002 | Boudreaux | A61L 2/10 422/24 |
| 6,524,529 B1 | 2/2003 | Horton, III | |
| 6,541,777 B1 | 4/2003 | Lombardo et al. | |
| 6,558,410 B1 | 5/2003 | Horton, III et al. | |
| 6,579,916 B1 * | 6/2003 | Askill | A61L 2/08 422/1 |
| 6,730,265 B2 | 5/2004 | Horton, III | |
| 6,737,020 B1 | 5/2004 | Horton, III et al. | |
| 6,766,097 B2 | 7/2004 | Horton, III | |
| 7,420,183 B2 | 9/2008 | Kaiser et al. | |
| 7,612,492 B2 | 11/2009 | Lestician | |
| 7,834,328 B2 | 11/2010 | Redmond et al. | |
| 7,888,657 B1 | 2/2011 | Zadro | |
| 7,950,818 B2 | 5/2011 | Klipstein et al. | |
| 8,197,087 B2 | 6/2012 | Sobue et al. | |
| 8,388,167 B2 | 3/2013 | Klipstein et al. | |
| 8,469,545 B2 | 6/2013 | Sobue et al. | |
| 8,556,950 B2 | 10/2013 | Rioux et al. | |
| 8,574,490 B2 | 11/2013 | Haytman et al. | |
| 8,585,681 B2 | 11/2013 | Boenig et al. | |
| 8,779,386 B2 | 7/2014 | Bak | |
| 9,295,742 B2 | 3/2016 | Rasooly et al. | |
| 9,492,574 B2 | 11/2016 | Rasooly et al. | |
| 2002/0063954 A1 | 5/2002 | Horton, III | |
| 2003/0017073 A1 * | 1/2003 | Eckhardt | A61L 2/10 422/24 |
| 2003/0086817 A1 | 5/2003 | Horton, III | |
| 2005/0244126 A1 * | 11/2005 | Howard | G02B 6/0096 385/133 |
| 2006/0195165 A1 * | 8/2006 | Gertner | A61N 5/0603 607/86 |
| 2007/0176117 A1 | 8/2007 | Redmond et al. | |
| 2008/0027399 A1 * | 1/2008 | Harding | A61M 39/045 604/265 |
| 2008/0051736 A1 * | 2/2008 | Rioux | A61L 2/084 604/265 |
| 2008/0191466 A1 * | 8/2008 | Knipple | A61M 16/0816 285/31 |
| 2008/0306454 A1 | 12/2008 | Sikora | |
| 2009/0012459 A1 | 1/2009 | Sobue et al. | |
| 2009/0250626 A1 | 10/2009 | Schlesser et al. | |
| 2011/0184382 A1 | 7/2011 | Cady | |
| 2011/0213339 A1 | 9/2011 | Bak | |
| 2012/0053512 A1 | 3/2012 | Muse | |
| 2012/0161032 A1 * | 6/2012 | Arcand | A61L 2/0047 250/454.11 |
| 2012/0321509 A1 | 12/2012 | Bak | |
| 2013/0267888 A1 * | 10/2013 | Rhodes | A61N 5/0624 604/21 |
| 2013/0323119 A1 | 12/2013 | Alwan | |
| 2013/0323120 A1 | 12/2013 | Ma | |
| 2014/0066703 A1 | 3/2014 | Blumenkranz | |
| 2014/0140888 A1 | 5/2014 | Neister | |
| 2014/0205498 A1 | 7/2014 | Bak | |
| 2014/0209923 A1 | 7/2014 | Xie et al. | |
| 2014/0264074 A1 | 9/2014 | Victor | |
| 2014/0334974 A1 * | 11/2014 | Rasooly | A61M 1/1696 422/24 |
| 2014/0341777 A1 * | 11/2014 | Deshays | A61L 2/24 422/24 |
| 2015/0165185 A1 | 6/2015 | Cohen | |
| 2015/0231287 A1 | 8/2015 | Lin et al. | |
| 2015/0352348 A1 | 12/2015 | Murphy-Chutorian et al. | |
| 2016/0077292 A1 * | 3/2016 | Dobrinsky | G02B 6/4239 385/38 |
| 2016/0082138 A1 | 3/2016 | Kermode et al. | |
| 2017/0072077 A1 | 3/2017 | Baker | |
| 2017/0119915 A1 * | 5/2017 | Lin | A61L 2/10 |
| 2017/0182305 A1 | 6/2017 | Kermode et al. | |
| 2017/0209608 A1 | 7/2017 | Cameron | |
| 2017/0232123 A1 * | 8/2017 | Burapachaisri | A61L 2/10 422/24 |

FOREIGN PATENT DOCUMENTS

| | | |
|---|---|---|
| WO | 2002102421 A1 | 12/2002 |
| WO | WO2008014437 A2 | 1/2008 |
| WO | WO2010023329 A1 | 3/2010 |
| WO | 2011107540 A1 | 9/2011 |
| WO | 2018013572 A1 | 1/2018 |
| WO | 2018013581 A1 | 1/2018 |
| WO | 2018089643 A1 | 5/2018 |

OTHER PUBLICATIONS

Song, et al., "Application of Ultraviolet Light-Emitting Diodes (UV-LEDS) for Water Disinfection: A Review", "Water Research", Mar. 2, 2016, pp. 341-349, vol. 94, Publisher: Elsevier Ltd., Published in: NL.

Hassett, et al., "Bacterial Adaptation to Oxidative Stress: Implications for Pathogenesis and Interaction With Phagocytic Cells", Dec. 1989, pp. 2574-2582, vol. 3, Publisher: The FASEB Journal, Published in: USA.

Venil, et al., "Bacterial Pigments and Their Applications", "Process Biochemistry", Jun. 10, 2013, pp. 1065-1079, vol. 48, Publisher: Elsevier Ltd., Published in: NL.

Nagae, et al., "Calculation of the Excitation Transfer Matrix Elements Between the S 2 or S 1 State of Carotenoid and the S 2 or S 1 State of Bacteriochlorophyll", "The Journal of Chemical Physics", Feb. 2, 1993, pp. 8012-8023, vol. 98, Publisher: AIP Publishing, Published in: USA.

Vatansever, et al., "Can Biowarfare Agents Be Defeated With Light?","Virulence", Nov. 15, 2013, pp. 796-825, vol. 4, No. 8, Publisher: Landes Bioscience, Published in: USA.

Wikipedia, "Carotenoid", "https://en.wikipedia.org/w/index.php?title=Carotenoid&oldid=697884880", Jan. 21, 2016, pp. 1-9, Publisher: Wikipedia, Published in: USA.

Sun, et al., "Collimating Lamp With Well Color Mixing of Red/Gree/Blue LEDS", "Optics Express", Jan. 2, 2012, pp. A75-A84, vol. 20, No. S1, Published in: USA.

Liu et al., "Color Me Bad: Microbial Pigments as Virulence Factors", "Cell Press", 2009, pp. 406-413, vol. 17, No. 9, Publisher: Elsevier Ltd., Published in: NL.

Esparza, "Color Patterns in a Tapered Lightpipe With RGB LEDS", "Current Developments in Lens Design and Optical Engineering XI; Advances in Thin Film Coatings VI", 2010, pp. 77860I-1-77860I-7, vol. 7786, Publisher: SPIE, Published in: USA.

Tang, et al., "A Comparative In Vitro Photoinactivation Study of Clinical Isolates of Multidrug-Resistant Pathogens", "J. Infect. Chemother.", Apr. 2007, pp. 87-91, vol. 13, No. 2, Publisher: The Japanese Association for Infectious Disease, Published in: JP.

Selby, et al., "A Cryptochrome/Photolyase Class of Enzymes With Single-Stranged DNA-Specific Photolyase Activity", "PNAS", Nov. 21, 2006, pp. 17696-17700, vol. 103, No. 47, Publisher: The National Academy of Sciences of the USA, Published in: USA.

Oguma, et al., "Determination of Pyrimidine Dimers in *Escherichia coli* and Cryptosporidium Parvum During UV Light Inactivation, Photoreactivation, and Dark Repair", "Applied and Environmental Microbiology", Oct. 2001, pp. 4630-4367, vol. 67, No. 10, Publisher: American Society for Microbiology, Published in: USA.

(56) References Cited

OTHER PUBLICATIONS

Ravanat, et al., "Direct and Indirect Effects of UV Radiation on DNA and Its Components", "Journal of Photochemistry and Photobiology", Aug. 10, 2001, pp. 88-102, vol. 63, Publisher: Elsevier Science B.V., Published in: NL.

Bak, et al., "Disinfection of Pseudomonas Aeruginosa Biofilm Contaminated Tube Lumens With Ultraviolet C Light Emitting Diodes", "Biofouling", Oct. 15, 2009, pp. 31-38, vol. 26, No. 1, Publisher: Taylor & Francis, Published in: UK.

Bak, et al., "Dose Requirements for UVC Disinfection of Catheter Biofilms", "Biofouling", Jan. 29, 2009, pp. 289-296, vol. 25, No. 3, Publisher: Taylor & Francis, Published in: UK.

Parada, et al., "Effects of MeV Proton Bombardment in Thin Film PFA and FEP Polymers", "Surface & Coatings Technology", Sep. 29, 2004, pp. 378-382, vol. 196, Publisher: Elsevier B.V., Published in: NL.

Bialka, et al., "Efficacy of Pulsed UV-Light for the Decontamination of *Escherichia coli* O157:H7 and *Salmonella* SPP. on Raspberries and Strawberries", "Food Microbiology and Safety", 2008, pp. M201-M207, vol. 73, No. 5, Publisher: Journal of Food Science, Published in: USA.

Li, et al., "Enhanced Germicidal Effects of Pulsed UV-LED Irradiation on Biofilms", "Journal of Applied Microbiology", Aug. 20, 2010, pp. 2183-2190, vol. 109, Publisher: The Society for Applied Microbiology, Published in: USA.

Lucas-Lledo, et al., "Evolution of Mutation Rates: Phylogenomic Analysis of the Photolyase/Cryptochrome Family", "Society for Molecular Biology and Evolution", Feb. 19, 2009, pp. 1143-1153, vol. 26, No. 5, Publisher: Oxford University Press, Published in: UK.

Novick, et al., "Experiements on Light-Reactivation of Ultra-Violet Inactivated Bacteria", Aug. 15, 1949, pp. 591-600, vol. 35, No. 1949, Publisher: Genetics, Published in: USA.

Wikipedia, "Flavonoid", "https://en.wikipedia.org/w/index.php?title=Flavonoids&oldid=699998877", Jan. 21, 2016, pp. 1-13, Publisher: Wikipedia, Published in: USA.

Carletti, et al., "Flavonoids and Melanins: A Common Strategy Across Two Kingdoms", "International Journal of Biological Sciences", Oct. 29, 2014, pp. 1159-1170, vol. 10, No. 10, Publisher: Ivyspring International Publisher, Published in: AU.

Stapleton, et al., "Flavonoids Can Protect Maize DNA From the Induction of Ultraviolet Radiation Damage", "Plant Physiol.", 1994, pp. 881-889, vol. 105, Publisher: American Society of Plant Biologists, Published in: USA.

Hijnen, et al., "Inactivation Credit of UV Radiation for Viruses, Bacteria and Protozoan (OO) Cysts in Water: A Review", "Water Research", Oct. 26, 2005, pp. 3-22, vol. 40, Publisher: Elsevier Ltd., Published in: NL.

Tyrrell, et al., "Interactions Between UV Radiation of Different Energies IKN the Inactivation of Bacteria", "Journal of Bateriology", Oct. 1978, pp. 437-440, vol. 136, No. 1, Publisher: American Society for Microbiology, Published in: USA.

Cheng, et al., "Irradiance Formations in Hollow Straight Light Pipes With Square and Circular Shapes", "J. Opt. Soc. Am. A", Feb. 2006, pp. 427-434, vol. 23, No. 2, Publisher: Optical Society of America, Published in: USA.

Cheng, et al., "Irradiance Formations of On-Axis Lambertian Point-like Sources in Polygonal Total-Internal-Reflection Straight Light Pipes", "J. Op. Soc. Am. A", Sep. 2007, pp. 2748-2757, vol. 24, No. 9, Publisher: Optical Society of America, Published in: USA.

Thiagarajan, et al., "Kinetics of Cyclobutane Thymine Dimer Splitting by DNA Photolyase Directly Monitored in the UV", Jun. 7, 2011, pp. 9402-9407, vol. 108, No. 23, Publisher: PNAS, Published in: USA.

Yin, et al., "Light Based Anti-Infectives: Ultraviolet C Irradiation, Photodynamic Therapy, Blue Light, and Beyond", "Current Opinion in Pharmacology", 2013, pp. 731-762, vol. 13, Publisher: Elsevier Ltd., Published in: NL.

Bosschaart, et al., "A Literature Review and Novel Theoretical Approach on the Optical Properties of Whole Blood", "Lasers Med Sci", Oct. 12, 2013, pp. 453-479, vol. 29, Publisher: Springer, Published in: DE.

Sanz, et al., "Modelling of Reactivation After UV Disinfection: Effect of UV-C Dose on Subsequent Photoreactivation and Dark Repair", "ScienceDirect", May 25, 2007, pp. 3141-3151, vol. 41, Publisher: Elsevier Inc., Published in: NL.

Siljegovic, et al., "Optical and Dielectric Properties of Fluorinated Ethylene Propylene and Tetrafluoroethylene-Perfluoro(Alkoxy Vinyl Ether) Copolymer Films Modified by Low Energy N4 and C4+ Ion Beams", "Radiation Physics and Chemistry", Aug. 30, 2011, pp. 1378-1385, vol. 80, Publisher: Elsevier Ltd., Published in: NL.

French, et al., "Optical Properties of Materials for Concentrator Photovoltaic Systems", 2009, pp. 000394-000399, Publisher: IEEE, Published in: USA.

Moreno, "Output Irradiance of Tapered Lightpipes", "J. Opt. Soc. Am. A", Sep. 2010, pp. 1985-1993, vol. 27, No. 9, Publisher: Optical Society of America, Published in: USA.

Cabiscol, et al., "Oxidative Stress in Bacteria and Protein Damage by Reactive Oxygen Species", "Internatl Microbiol", 2000, pp. 3-8, vol. 3, Publisher: Springer-Verlag Iberica, Published in: DE.

Jori, et al., "Photodynamic Therapy in the Treatment of Microbial Infections: Basic Principles and Perspective Applications", "Lasers in Surgery and Medicine", Jun. 19, 2006, pp. 468-481, vol. 38, Publisher: Wiley InterScience, Published in: USA.

Yoshii, et al., "Photo-Excitation of Carotenoids Causes Cytotoxicity via Singlet Oxygen Production", "Biochemical and Biophysical Research Communication", 2012, pp. 640-645, vol. 417, Publisher: Elsevier Inc., Published in: NL.

"Photolyase", "https://en.widipedia.org/w/index.php?title=Photolyase&oldid=684658970", Oct. 8, 2015, pp. 1-4, Publisher: Wikipedia, Published in: US.

Ren, et al., "Photo-Oxidation of 6-Thioguanine by UVA: The Formation of Addition Products With Low Molecular Weight Thiol Compounds", "Photochemistry and Photobiology", May 14, 2010, pp. 1038-1045, vol. 86, Publisher: The American Society of Photobiology, Published in: USA.

Bak, et al., "Potential In Vivo UVC Disinfction of Catheter Lumens: Estimation of the Doses Received by the Blood Flow Outside the Catheter Tip Hole", "Photochemistry and Photobiology", Dec. 20, 2010, pp. 350-356, vol. 87, Publisher: The American Society of Photobiology, Published in: USA.

Zimmer, et al., "Potential Repair of *Escherichia coli* DNA Following Exposure to UV Radiation From Both Medium- and Low-Pressure UV Sources Used in Drinking Water Treatment", "Applied and Environmental Microbiology", Jul. 2002, pp. 3293-3299, vol. 68, No. 7, Publisher: American Society for Microbiology, Published in: USA.

Bank, et al., "A Prototype Catheter Designed for Ultraviolet C Disinfection", "Journal of Hospital Infection", Mar. 3, 2013, pp. 173-177, vol. 84, Publisher: Elsevier, Published in: USA.

Wengraitis, et al., "Pulsed UV-C Disinfection of *Escherichia coli* With Light-Emitting Diodes, Emitted at Various Repetition Rates and Duty Cycles", "Photochemistry and Photobiology", 2013, pp. 127-131, vol. 89, Publisher: The American Society of Photobiology, Published in: USA.

Zhao, et al., "Reactive Oxygen Species and the Bacterial Response to Lethal Stress", "Curr. Opin. Microbiol.", Oct. 2014, pp. 1-12, Publisher: Elseiver, Ltd., Published in: NL.

Cassarly, "Recent Advances in Mixing Rods", "Illumination Optics", 2008, pp. 710307-1-710307-10, vol. 7103, Publisher: SPIE, Published in: USA.

Roberts, et al., "Recovery From Ultraviolet Irradiation in *Escherichia coli*", Dec. 28, 1948, pp. 363-375, vol. 57, Publisher: Department of Terrestial Magnetism, Carnegie Institute of Washington, Published in: USA.

Kari, et al., "Reliability of Point Source Approximations in Compact LED Lens Designs", "Optics Express", Nov. 7, 2011, pp. A1190-A1195, vol. 19, No. S6, Published in: USA.

Saw, "Science Against Microbial Pathogens: Photodynamic Therapy Approaches", 2011, pp. 668-674, Publisher: Formatex, Published in: USA.

(56) References Cited

OTHER PUBLICATIONS

Aihara, et al., "Simultaneous Irradiation With Different Wavelengths of Ultraviolet Light Has Synergistic Bactericidal Effect on Vibrio Parahaemolyticus", "Photochemistry and Photobiology", Apr. 17, 2014, pp. 1-38, Publisher: American Society of Photobiology, Published in: USA.

Oreski, et al., "Determination of Solar Optical Properties of Transparent Polymer Films Using UV/VIS Spectroscopy", "Solar Energy Materials & Solar Cells", Feb. 6, 2010, pp. 884-891, vol. 94, Publisher: Elsevier B.V., Published in: NL.

Liu, et al., "*Staphylococcus aureus* Golden Pigment Impairs Neotrophil Killing and Promotes Virulence Through Its Antioxidant Activity", "JEM", Jul. 11, 2005, pp. 209-215, vol. 2202, No. 2, Publisher: The Rockefeller University Press, Published in: USA.

Sancar, "Structure and Function of DNA Photolyase and Cryptochrome Blue-Light Photoreceptors", "Chem. Rev.", Apr. 19, 2003, pp. 2203-2237, vol. 103, Publisher: American Chemical Society, Published in: USA.

Qiu, et al., "Survival of Shewanella Oneidensis MR-1 After UV Radiation Exposure", "Applied and Environmental Microbiology", Nov. 2004, pp. 6435-6443, vol. 70, No. 11, Publisher: American Society for Microbiology, Published in: USA.

Dai, et al., "Ultraviolet-C Irradiation for Prevention of Central Venous Catheter-Related Infections: An In Vitro Study", "Photochemistry and Photobiology", 2011, pp. 250-255, vol. 87, Publisher: The American Society of Photobiology, Published in: USA.

Wikipedia, "Ultraviolet Germicidal Irradiation", "https://en.wikipedia.org/w/index.php?title=Ultraviolet_germicidal_irradiation&oldid=689183127", Jan. 21, 2016, pp. 1-10, Publisher: Wikipedia, Published in: USA.

Cadet, et al., "Ultraviolet Radiation-Mediated Damage to Cellular DNA", "Mutation Research", Jan. 26, 2005, pp. 3-17, vol. 571, Publisher: Elsevier B.V., Published in: NL.

Bak, et al., "A UVC Device for Intro-Luminal Disinfection of Catheters: In Vitro Tests on Soft Polymer Tubes Contaminated With Pseudomonas Aeruginosa, *Staphylococcus aureus*, *Escherichia coli* and Candida Albicans", "Photochemisty and Photobiology", Jun. 8, 2011, pp. 1123-1128, vol. 87, Publisher: The American Society of Photobiology, Published in: USA.

Bak, et al., "UVC Fluencies for Preventative Treatment of Pseudomonas Aeruginosa Contaminated Polymer Tubes", "Biofouling", Sep. 20, 2010, pp. 821-828, vol. 26, No. 7, Publisher: Taylor & Francis, Published in: UK.

Kowalski, "UVGI Disinfection Theory", "Ultraviolet Germicidal Irradiation Handbook", 2009, pp. 17-50, Publisher: Springer-Verlag Berlin Heidelberg, Published in: DE.

Sinha, et al., "UV-Induced DNA Damage and Repair: A Review", "Photochem. Photobiol. Sci.", Mar. 13, 2002, pp. 225-236, vol. 1, Publisher: The Royal Society of Chemistry and Owner Societies, Published in: UK.

Ehling-Schultz, et al., "UV Protection in Cyanobacteria", "European Journal of Phycology", Jun. 3, 2010, pp. 329-338, vol. 34, Publisher: Taylor & Francis, Published in: EP.

Ashley et al., "Effect of UV Light on Disinfection of Peritoneal Dialysis Catheter Connections", "Peritoneal Dialysis International", Jan. 2017, pp. 109-111, vol. 37, No. 1, Published in: Canada.

\* cited by examiner

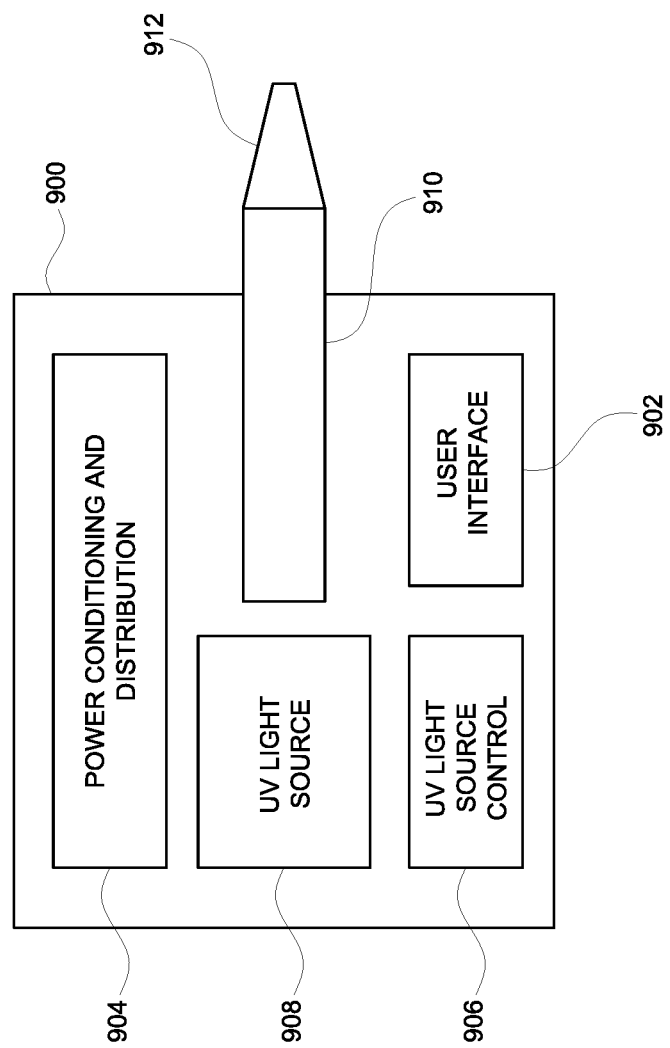

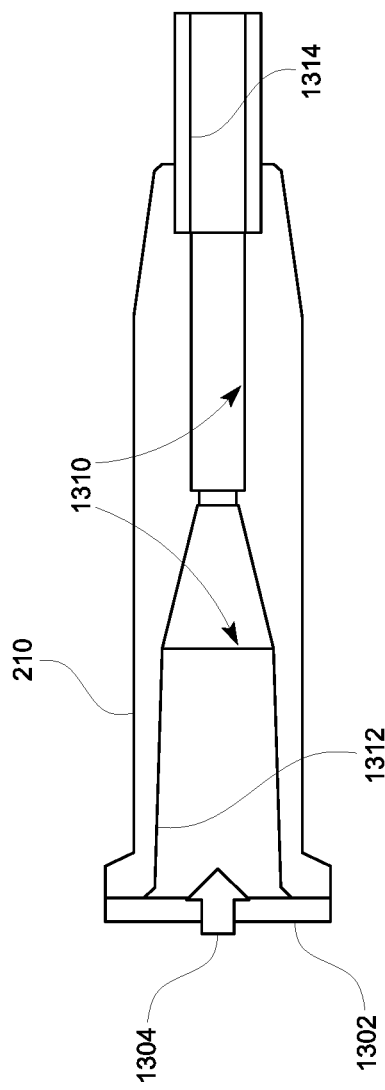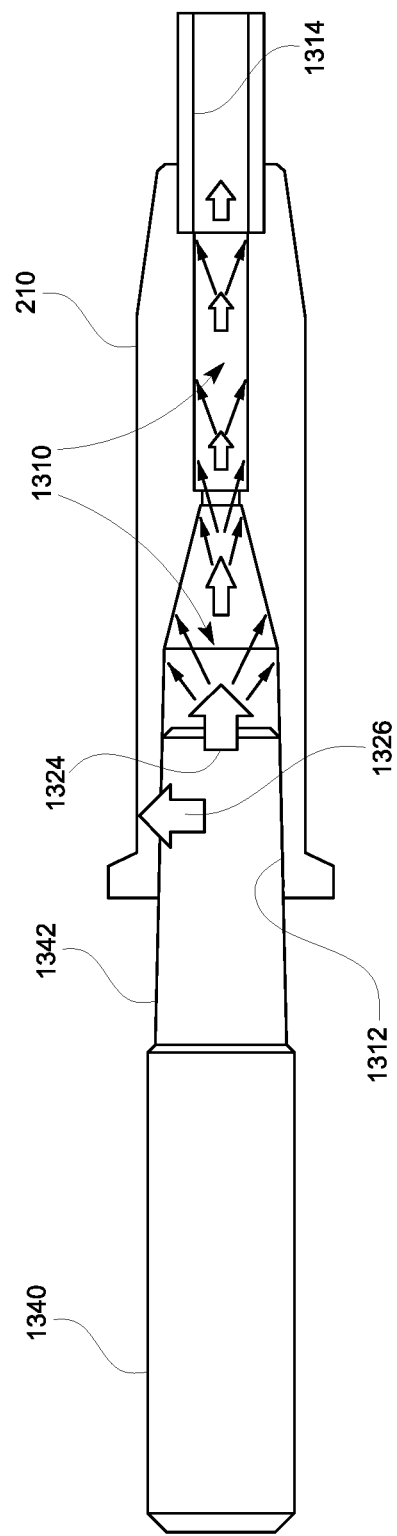
FIG.13A
FIG.13B

SYSTEM AND METHOD FOR STERILIZATION USING ULTRAVIOLET RADIATION

FIELD OF THE INVENTION

The present disclosure relates to sterilization using ultraviolet radiation.

BACKGROUND OF THE INVENTION

The golden age of antibiotic discovery occurred from 1950 to 1970, whereafter the consensus outside the microbiology community was that the war on pathogenic microbes was over. Over forty years later it is apparent the war against infectious microorganisms continues and the growing rate of resistance among pathogens in both the hospital and community environment represents a serious medical crisis.

Every year over 13 million deaths worldwide are attributed to the emergence of new infectious disease or to the reemergence of diseases previously controlled and which can be attributed to drug resistance. Infections linked to healthcare practices are particularly concerning. Using the most recent data available, the CDC in 2011 reported, based upon a survey of 183 hospitals throughout 2010, that, on any given day while receiving acute care, 1 in 25 patients will contract a hospital acquired infection (HAI). This corresponded to 722,000 HAIs in 2010 and carried a mortality rate of greater than 10%. These infections cost the U.S. healthcare system billions of dollars each year and lead to the loss of tens of thousands of lives.

One of the most challenging microbes to treat is Methicillin Resistant *Staphylococcus aureus* (MRSA), where infections account for up to 50% of both nosocomial and community-associated staphylococcal infections. The MRSA incidence in US intensive care has skyrocketed from 2% in 1974 to 64% by 2004. A plethora of disease states are caused by MRSA; it is found to be among the most frequently identified pathogens causing pneumonia, and is associated with increased morbidity and mortality rates, where it accounts for 20%-40% of all hospital-acquired pneumonia (HAP) and ventilator-associated pneumonia (VAP). It causes skin and soft tissue infections (SSTIs), such as diabetic MRSA wound infections, leads to increased costs, prolongs healing time and contributes to an unfavorable prognosis. MRSA infections may also be associated with persistent or recurrent bacteremia especially in long-term hemodialysis patients with renal disease. Persistent MRSA bacteremia is associated with infective endocarditis eventually leading to heart failure and even death. Bone infections constitute another difficult-to-treat clinical entity, with diabetes and peripheral vascular disease predisposing patients to MRSA osteomyelitis.

Catheters represent a ubiquitous component in the healthcare environment and are used to administer therapeutics (chemotherapy agents, antibiotics, pharmaceuticals, blood, and the like) during routine treatment of patients including those diagnosed with a chronic disease state requiring long term care. Central line-associated bloodstream infections (CLABSIs) are one of the deadliest types of HAIs, with a mortality rate of 12%-25%. Encouragingly, due to directed efforts against this problem, the incidence of CLABSI appears to be on the decline with an overall 46% decrease between 2008 and 2013. This corresponds to approximately 6,000 lives saved and $414 million in potential excess healthcare costs in 2009 and approximately $1.8 billion in cumulative excess healthcare costs since 2001. Despite this downward trend in mortality, MRSA still remains a globally significant public health threat. Globally, key factors contributing to this problem are healthcare practices, human factors, an immunocompromised or immunodeficient population, and highly virulent, antibiotic-resistant pathogens. The rise of antibiotic "superbugs" is a direct result of antibiotic overuse.

This rise in life-threatening drug resistant pathogens, not limited solely to MRSA, has increased the need for new classes of antibiotics against both hospital-acquired and community-acquired pathogens, with urgent need to treat *Enterococcus faecalis, Staphylococcus aureus, Acinetobacter baumannii, Klebsiella pneumoniae, Pseudomonas aeruginosa,* and *Enterobacter* species.

These pathogens are dubbed ESKAPE pathogens to emphasize that they currently cause the majority of US hospital infections and effectively "escape" the effects of antibacterial drugs. For example, more people die in US Hospitals of methicillin-resistant *S. aureus* (MRSA) than HIV/AIDS and tuberculosis combined. The problem has become so dire that clinicians are forced to use older, previously discarded drugs such as colistin, associated with significant toxicity, and this current climate does not bode well for the aging baby-boomer generation, immunocompromised patients, patients undergoing surgery, transplantation, and chemotherapy, nor the increasing number of neonatal patients in intensive care, all of whom are at increased risk to infections by drug resistant pathogens.

*Streptococcus pneumoniae* results in 40,000 deaths in the US each year and by 1999 25% of all US isolates were penicillin resistant with small children and the elderly at an increased risk.

*Pseudomonas* is an opportunistic pathogen, causes fatal wound infections, burn infections, and chronic infections of the lungs in cystic fibrosis patients. Few antibiotics inhibit this pathogen although the organism rarely infects non-compromised patients. *Pseudomonas* is capable of colonizing practically any tissue of patients compromised in some manner. It also causes urinary tract infections, respiratory system infections, dermatitis, soft tissue infection, bacteremia, bone and joint infections, gastrointestinal infections and a variety of other disease states.

In addition to MRSA, VRSA (vancomycin resistant *S. aureus*) and VISA (vancomycin intermediate *S. aureus*) strains also pose an important threat to second-line treatments for MRSA. The first report of VRSA in Europe was published last year from Portugal. Resistance to linezolid and daptomycin has also been documented.

In some locations, candidaemia is the most common cause of all bloodstream infections related to vascular catheters. Inappropriate antifungal therapy is associated with increased mortality, increased attributable costs, and increased burden of fluconazole non-susceptible *Candida* species. *Candida* is associated with a mortality rate of ~35% and higher treatment costs and length of hospitalization. Patients with resistant infections may experience delay in receiving appropriate therapy, which can increase costs, length of stay, and morbidity and mortality. In 2005, CDC estimated that each case of *Candida* infection results in 3-13 days of additional hospitalization, and incurs a total of US$6,000 to US$29,000 in direct health-care costs. Based on current data and projections, these infections add a total of US$8 billion to US health-care expenditures every year.

According to the World Health Organization, it is suspected that resistant infections greatly increase these costs. However, few data exist on the economic impact of resistant Candida infections. Candida infections are a persistent and increasingly important public health problem, particularly for vulnerable populations such as cancer patients, dialysis patients, transplant recipients, and in neonates and other patients in intensive care units. In some locations, half of all infections are resistant to first-line therapy. Resistance to azoles is probably increasing, and resistance to the echinocandins is emerging. It is likely that the global burden will increase with increasing populations of immunocompromised patients as economies develop and health care improves. Given these changes, it is critically important to have active surveillance activities for resistance trends in Candida infections, to determine the burden of infections due to antifungal-resistant Candida, its economic impact, and possible areas where prevention and control strategies can be focused.

This trend in resistance has spurred a new crisis, the "antibiotic crisis" and has gained the attention of the United States Congress, which has partnered with the Infectious Diseases Society of America (IDSA), the Food and Drug Administration (FDA), the National Institutes of Health (NIH), the Center for Disease Control (CDC), and other stakeholder groups to highlight this problem. Alarmingly, despite mobilization of funds and resources, only two new classes of antibiotic have been introduced into the market over the past 30 years. Overall, the consumption rate of antibiotics has been on a steady decline, with trends strongest in France and Japan where antibiotic usage between 2000 and 2009 decreased by 21% and 15%, respectively, as clinicians fear usage will further promote the rise in antibiotic resistant "superbugs."

The CDC has stated there is a consensus to eliminate HAIs. Alternative strategies, designed to reduce the incidence of infection, represent an expanding area for the development of new treatment modalities, a necessity as existing antibiotics continue to fail against formerly susceptible pathogens.

SUMMARY OF THE INVENTION

This invention provides a method and apparatus for a chemical-free, non-drug approach to killing germs with UV light, and in particular germs associated with indwelling catheters and catheter attachment systems, including Luer systems, and other attachment systems.

An optical plug for sterilizing a female Luer fitting can include an insertion end having an insertion sidewall and a front window at a proximal end of the insertion end, and a base end having a base window at a distal end of the base end, whereby light can enter the base window and exit through the insertion sidewall and the front window. Furthermore, the base end sidewall(s) can be designed so that light rays within the base end are transmitted through the length of the base end via multiple internal reflections, allowing the base end to be of arbitrary length.

The insertion end of the optical plug can be axisymmetric. The insertion end can also include a bezel or fillet between the insertion sidewall and the front window. This insertion end bezel can have an angle of approximately 93.4°, or an angle of approximately 47° from the central axis of the optical plug. The insertion end can have a diameter in the range of approximately 3.925 mm to 4 mm where the insertion sidewall meets the bezel. The insertion sidewall can be frustoconical with an approximately 6% slope. The optical plug can be comprised of a fused silica quartz. The insertion sidewall and the front window can be ground to an approximately 1500 grit surface finish.

The base end of the optical plug can be axisymmetric. The base end can also include a bezel or fillet between the base sidewall and the base window. This base end bezel can have an angle of approximately 90°, or an angle of approximately 45° from the central axis of the optical plug. The base end cross section can be circular or in the shape of a regular polygon such as a hexagon. The base sidewall can be polished to a smooth optical surface finish to enable total internal reflection of internal light rays incident on its sidewall surfaces.

A sterilizer for sterilizing a female Luer fitting can include an optical plug, the optical plug including a base end, an insertion end, and a front window at a proximal end of the insertion end, wherein the insertion end is adapted to be inserted into the female Luer fitting. The sterilizer can also include a sterilizer body, the body including a catheter harness and a female Luer fitting harness. The sterilizer can also include at least one UV light source, wherein UV light can be radiated through the optical plug, thereby sterilizing the female Luer and at least a portion of a catheter. The sterilizer can also include a means of supplying power to the at least one UV light source, wherein the means of supplying power can be an internal power source, such as a battery, combined with electronics for conditioning/converting and distributing electrical power to electrical/optoelectronic components within the sterilizer, or the means of supplying power can be a connection to an external electrical power source combined with electronics for conditioning/converting and distributing electrical power to components within the sterilizer. The sterilizer can also include a means of controlling/adjusting the light output of the at least one UV light source. The sterilizer can also include a means of self-calibrating the light output of the at least one UV light source, wherein the light output of the at least one UV light source is measured and then adjusted accordingly to maintain a desired light output level.

The catheter harness can prevent ambient light from entering into the catheter and its female Luer fitting. The at least one UV light source can be a UV-C light source. The UV-C light source can provide light in a range of approximately 250 nm to 280 nm. The at least one light source can be a UV-C light source and a UV-A light source. The UV-C light source can provide light in a range of approximately 250 nm to 280 nm, and the UV-A light source can provide light in a range of approximately 315 nm to 400 nm.

A method of sterilizing a female Luer fitting and a catheter attached to the female Luer fitting can include inserting an insertion end of an optical plug into the female Luer fitting, placing the catheter into a catheter harness of a sterilizer, placing the female Luer fitting into a female Luer fitting harness of the sterilizer, closing the sterilizer, and turning on at least one UV light source, so that UV light enters the optical plug and irradiates the female Luer fitting and the catheter.

The at least one UV light source can be a UV-C light source. The UV-C light source can emit light in a range of approximately 250 nm to 280 nm. The at least one UV light source can be a UV-C light source and a UV-A light source. The UV-C light source can emit light in a range of approximately 250 nm to 280 nm, and the UV-A light source can emit light in a range of approximately 315 nm to 400 nm.

BRIEF DESCRIPTION OF THE DRAWINGS

The invention description below refers to the accompanying drawings, of which:

FIG. 9 is a schematic diagram of exemplary components of a sterilizer, according to an embodiment;

FIG. 13A shows light entering a female Luer fitting without an optical plug;

FIG. 13B shows light entering a female Luer fitting through an optical plug;

DETAILED DESCRIPTION

The combination of UV-A and UV-C light together can have a synergistic sterilizing effect. The effect of the two light wavelengths together can be greater than the sum of each light wavelength individually. UV-A light, for example in a range of approximately between 315 nm and 400 nm, and by way of further example in a range of approximately between 360 nm and 370 nm, can induce cells to increase production of pigments such as antioxidants and porphyrins and other proteins that protect against damage to the cell from terrestrial UV light such as UV-A and UV-B. By way of non-limiting examples, these pigments can include porphyrin, carotenoids, melanins, xanthomonadin, ferritin, luteine, cytochromes, spirilloxanthin, chlorobactene, and lycopene.

Figure 1B:
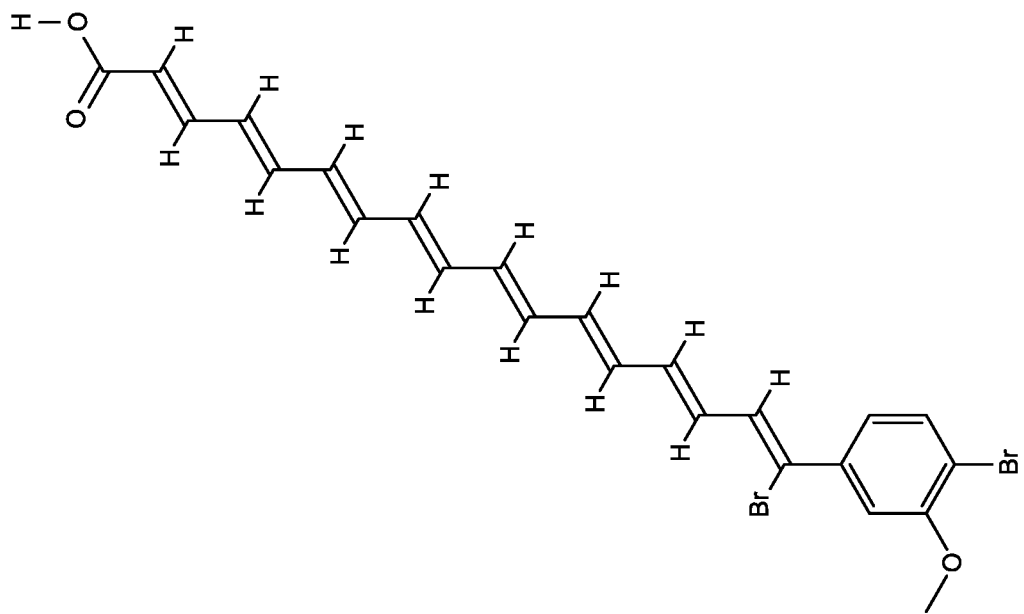
FIG. 1B is a structural diagram of Xanthomonadin, an exemplary pigment endogenous to bacteria.
Figure 1A:
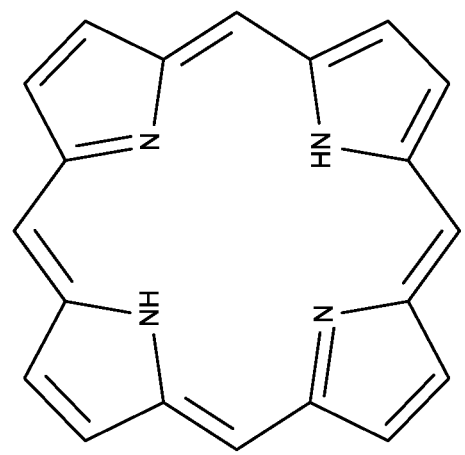
FIG. 1A is a structural diagram of Porphyrin, an exemplary pigment endogenous to bacteria.

FIG. 1A is a structural diagram of porphyrin, an exemplary pigment endogenous to bacteria. These endogenous pigments arise within a bacterium, however it should be noted that this is only one of many pigments that are produced within the bacterial kingdom. Each species of bacteria can make many different kinds of pigments, and pigments between species differ.

Figure 1C:
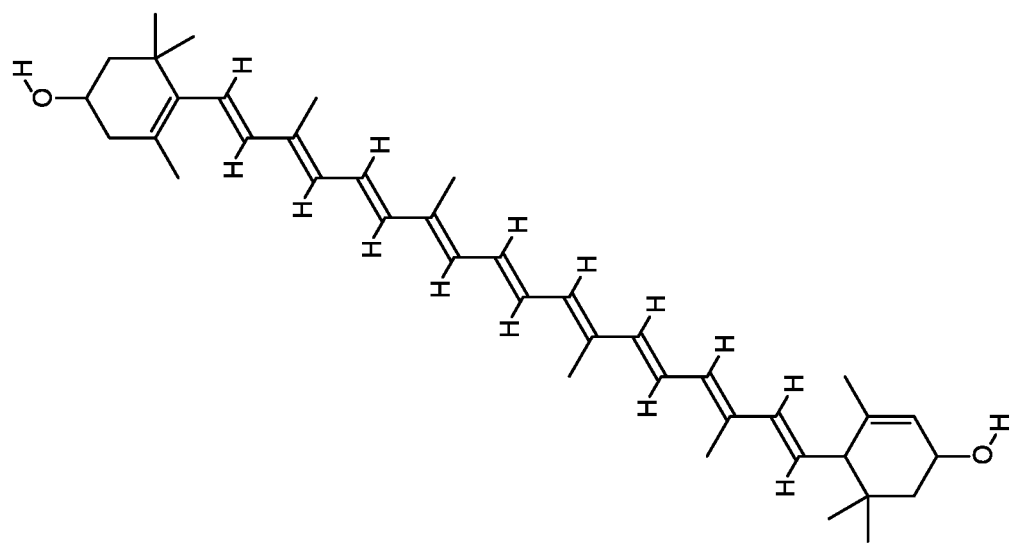
FIG. 1C is a structural diagram of luteine, an exemplary pigment endogenous to bacteria.
Figure 1D:
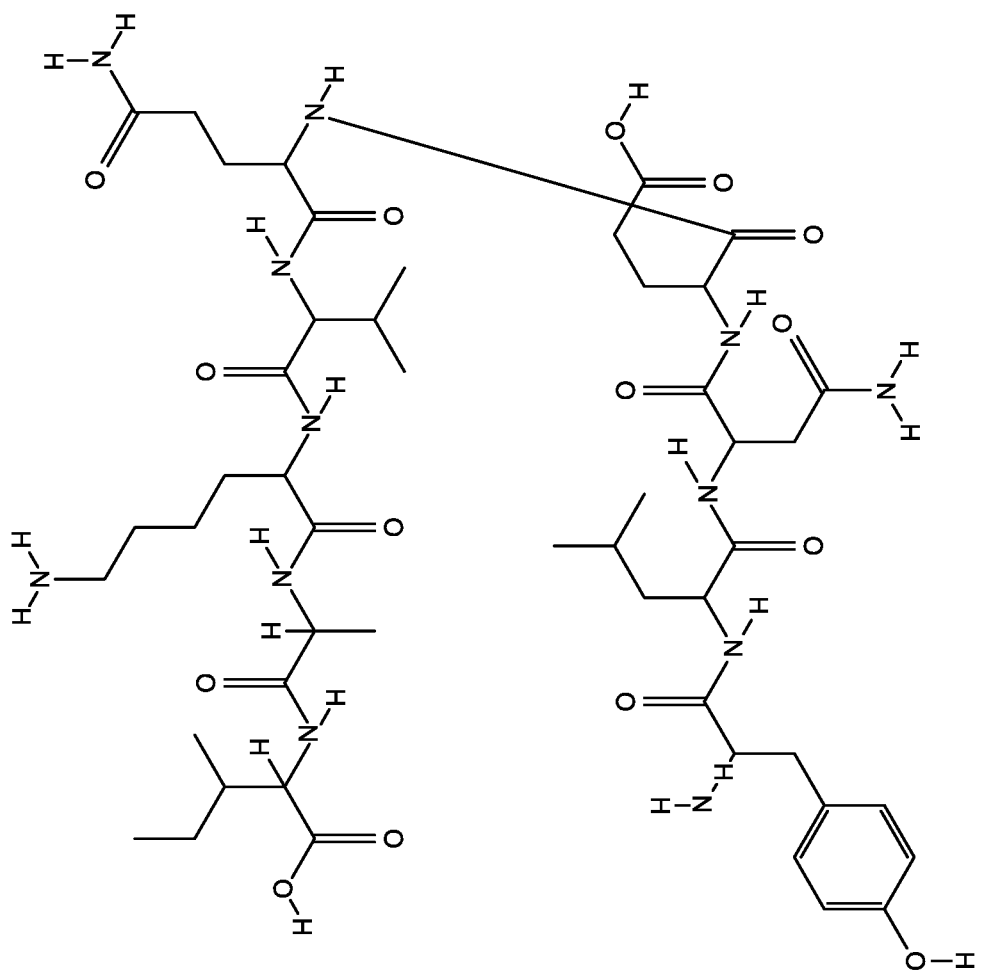
FIG. 1D is a structural diagram of ferritin, an exemplary pigment endogenous to bacteria.
Figure 1F:
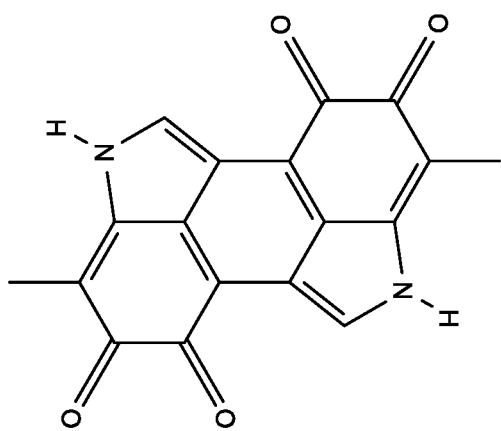
FIG. 1F is a structural diagram of melanin, an exemplary pigment endogenous to bacteria.
Figure 1E:
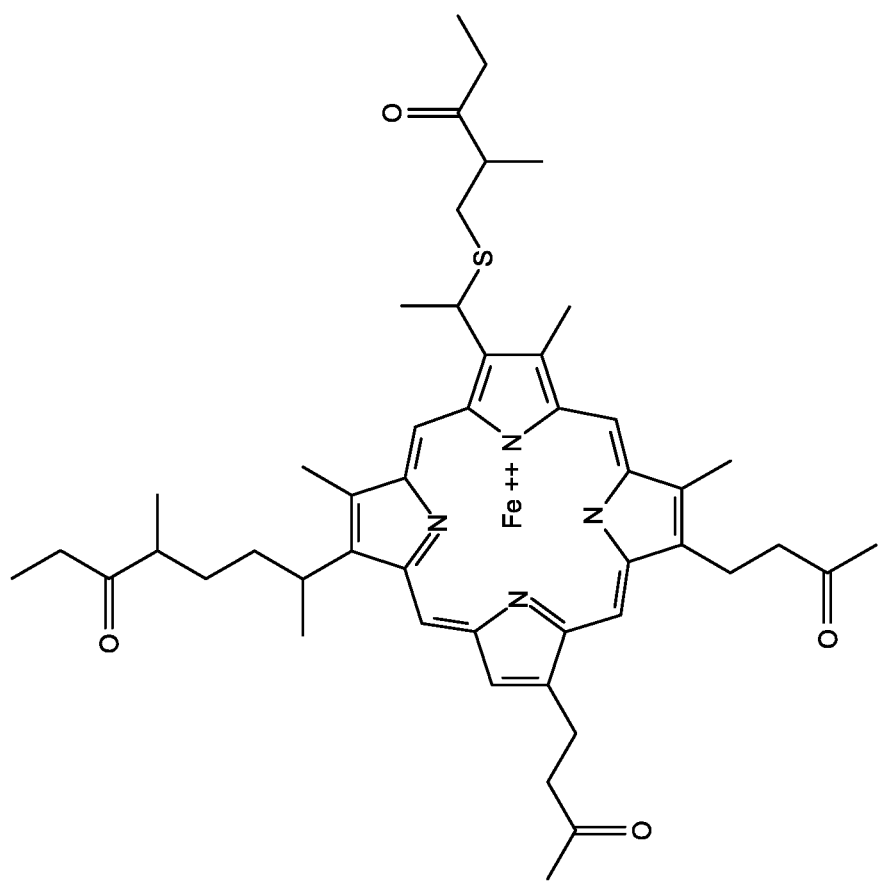
FIG. 1E is a structural diagram of cytochromes, an exemplary pigment endogenous to bacteria.
Figure 1G:
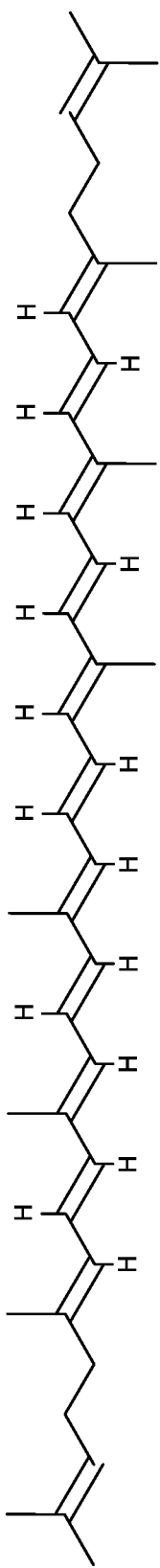
FIG. 1G is a structural diagram of lycopene, an exemplary pigment endogenous to bacteria.
Figure 1H:
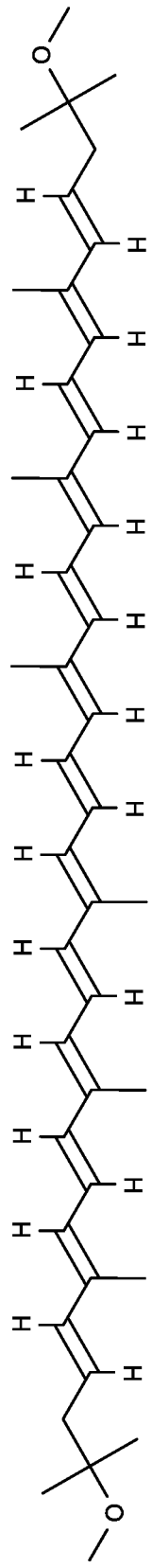
FIG. 1H is a structural diagram of spirilloxanthin, an exemplary pigment endogenous to bacteria.
Figure 1I:
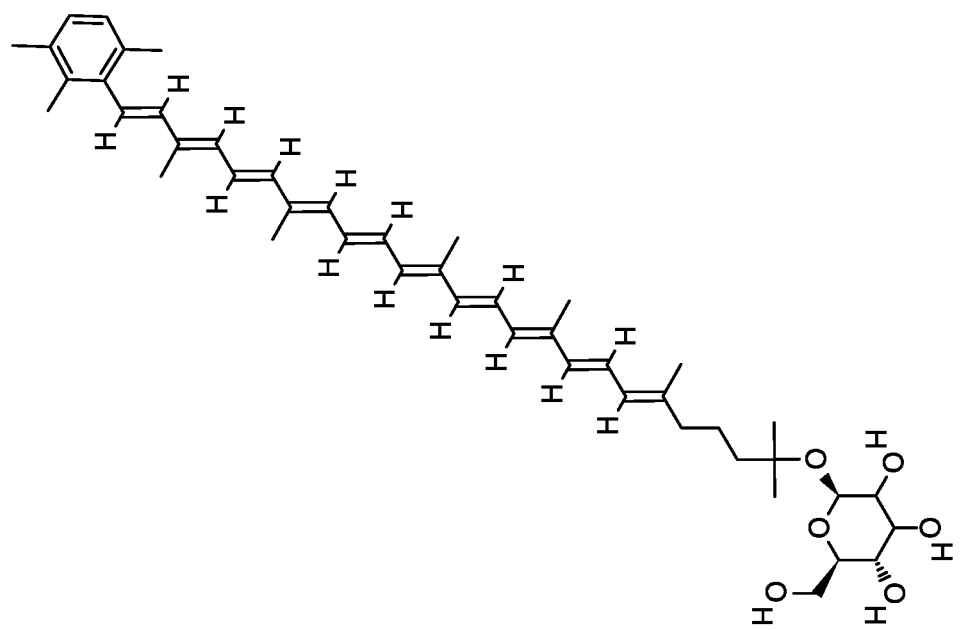
FIG. 1I is a structural diagram of chlorobactene, an exemplary pigment endogenous to bacteria.

By way of non-limiting examples, FIGS. 1B-1I show a variety of different pigments that occur naturally in bacteria. FIG. 1B is a structural diagram of xanthomonadin, an exemplary pigment endogenous to bacteria. FIG. 1C is a structural diagram of luteine, an exemplary pigment endogenous to bacteria. FIG. 1D is a structural diagram of ferritin, an exemplary pigment endogenous to bacteria. FIG. 1E is a structural diagram of cytochromes, an exemplary pigment endogenous to bacteria. FIG. 1F is a structural diagram of melanin, an exemplary pigment endogenous to bacteria. FIG. 1G is a structural diagram of lycopene, an exemplary pigment endogenous to bacteria. FIG. 1H is a structural diagram of spirilloxanthin, an exemplary pigment endogenous to bacteria. FIG. 1I is a structural diagram of chlorobactene, an exemplary pigment endogenous to bacteria.

All of these pigments shown in FIGS. 1A-1I contain a chromophore. When a chromophore within the pigment absorbs a sufficient dose of UV light, a Reactive Oxygen Species (ROS) is liberated. UV light, including UV-A and UV-C light, can convert the pigments produced in response to a UV-A light, such as pigment 200, into photoreactive byproducts, such as free radicals and other damaging byproducts. Because of the shorter wavelength, UV-C can convert the pigments into the photoreactive byproducts more efficiently, or with less energy. The UV-C light can cause the atoms in the pigments (chromophores) to get excited to the point that they can become phototoxic by-products (also called reactive oxygen species, ROS). The UV light, including UV-A and UV-C light, can thereby poison the cell through its own innate defense mechanism to UV-A light, so that the cell is killed by its own defense system. The net effect can be that the cell is tricked into preparing against one type of damage from the UV-A light, and then the cell's own defenses can be used against it with exposure to UV-C light. This effect combined with the DNA damage caused by UV-C light can synergistically render the cell unable to maintain viability. The DNA damage can include, by way of non-limiting examples, lesions in DNA induced by UV light, including the cyclobutane pyrimidine dimers (CPD) and the pyrimidine-pyrimidone photoproduct [6-4]. UV radiation induces DNA lesions (CPDs) and 6-4 photoproducts (6-4PPs) and their Dewar valence isomers. In addition to DNA damage and conversion of chromophores to ROS, other types of UV induced photodamage contributing to synergistic lethality include any toxic photoproduct resulting from photo oxidation against intracellular aldehydes, ketones, and carboxylic acids. Photodamage from UV light can also include damage to cellular membranes and cell walls. Any survivors of the treatment should be inherently less virulent since one of the functions of pigmentation is virulence; specifically, under normal conditions, the pigments serve as antioxidants to ROS, however in this treatment scheme, the pigment is instead coopted to become a ROS itself. The combination of UVA and UVC irradiation treatment has a synergetic effect on the killing of bacteria and yeast, especially on the surface of a biofilm. This system of combined UV-C and UV-A radiation can be effective against fungi, bacteria, parasites, and viruses. The body uses peroxides to kill the remaining bacteria, and the sick and bleached bacteria become susceptible to the peroxides, resulting in additional synergistic lethality.

The effectiveness of the use of UV light to kill microorganisms may be influenced by many factors, including the wavelength used, the energy (calculated as Power (W)×time (s)=Energy (J)), the irradiance (calculated as Power (W)/Area ($m^2$)=Irradiance), and the radiant exposure (calculated as Energy (J)/$m^2$=radiant exposure). Other factors can increase effectiveness, such as an engineered light structure. This engineered light structure can include a duty cycle and pulse frequency. Microorganisms can have a photoreactivation mechanism whereby they can better recover from UV photodamage when they are exposed to visible light following UV photodamage, so effectiveness of the treatment can be also increased by minimizing exposure of the treated surfaces to ambient light following the UV treatment. By way of non-limiting example, ambient light can stimulate photolyase to repair DNA lesions caused by the UV light treatment (repair of the CPD). Repairing the damaged DNA lesions is required for cellular transcription, which is a necessary part of cellular replication. Blocking ambient light is one way to prevent photoreactivation in microorganisms upon exposure to DNA damage, and thereby prevent cellular replication.

When a sufficient dose of UV light irradiates all surfaces to be disinfected, UV light can be effective at killing microorganisms. UV light may be used for sterilization in many applications, including sterilizing indwelling catheters in patients. However, for UV light to be effective, it is necessary for the UV light to irradiate the interior surfaces of the indwelling catheter with a sufficient dose of UV light. Surfaces that do not receive a sufficient dosage of UV light may not be fully sterilized.

Figure 2:
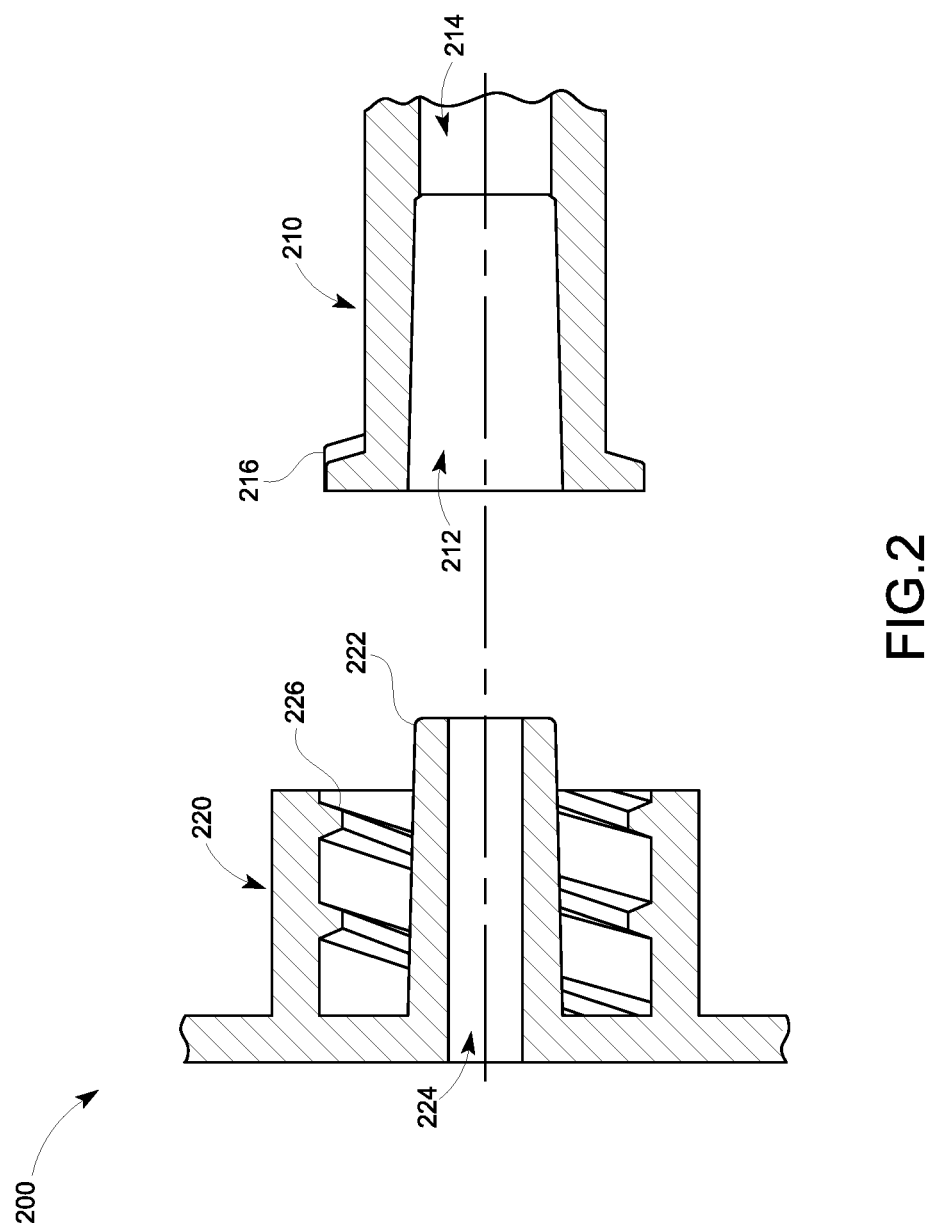
FIG. 2 is a cross-section of a standard ISO 594 Luer system.

FIG. 2 is a cross-section of a standard ISO 594 Luer system. A standard Luer system 200 can have a female Luer fitting 210 and a male Luer fitting 220. The female Luer fitting 210 is adapted to mate with the male Luer fitting 220. Male Luer fitting 220 has an insertion end 222 adapted for insertion into an internal cavity 212 of the female Luer fitting 210. Both the male insertion end 222 and the female internal cavity 212 have an approximately 6% slope. The male insertion end is wider at the base and narrower at the end, with an approximately 6% slope, and the female internal cavity has a corresponding shape and 6% slope, so that the two parts can mate together snugly. Male Luer fitting 220 has a male lumen 224 through the male fitting 220, and female Luer fitting 210 has a female lumen 214 through the female fitting 210, so that when the two parts are mated together fluid can flow through one lumen to the other without leakage. The male Luer fitting 220 has threads 226 adapted to be engaged by tabs 216 on the female Luer fitting 210. Indwelling catheters can have a female Luer fitting 210 at the end of the catheter. A medical professional can prepare, for example, a IV drip with a male Luer fitting 220 at the end of an IV tube, and can quickly attach the male Luer fitting 220 to the female Luer fitting 210 at the end of an indwelling catheter, and can begin an IV drip into the patent without having to introduce a new tube into the patent. Over time, a biofilm can build up on the inside surfaces of the Luer fitting and the attached catheter. To avoid introduction of pathogens into the patent, including from biofilms within the internal cavity 212, it is necessary to sterilize the internal cavity 212 of the female Luer fitting 210 and at least a portion of the attached catheter before fluids can be passed through them and into the patient.

Figure 3A:
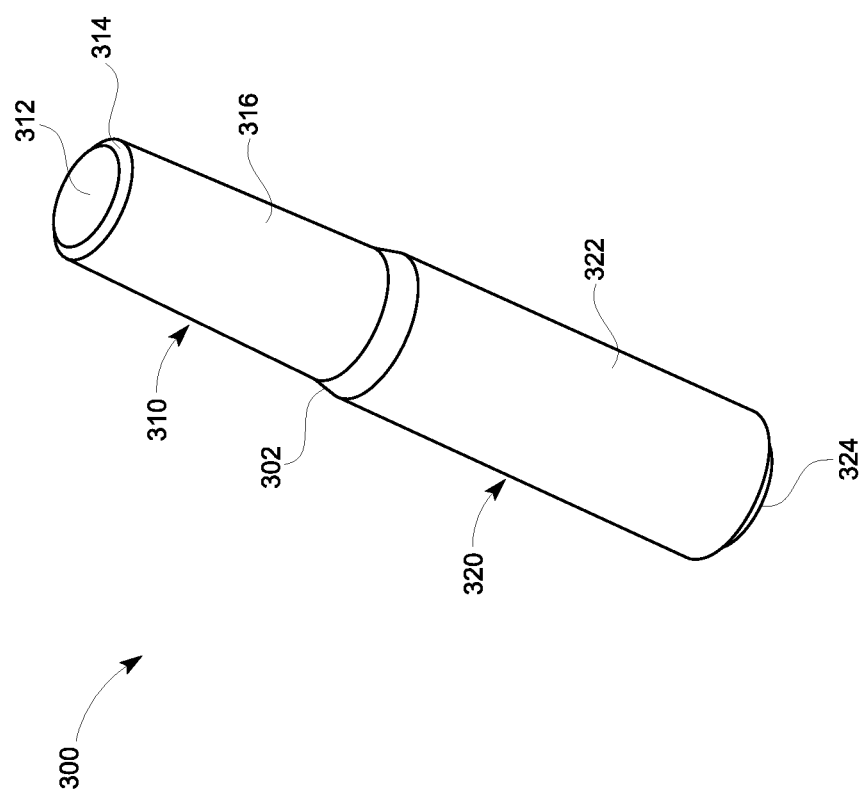
FIG. 3A is perspective view of an optical plug, according to an embodiment.

FIG. 3A is perspective view of an optical plug, according to an embodiment. Optical plug 300 is ISO 594 compatible, and can be inserted into an ISO 594 female Luer fitting, allowing UV light to be introduced into a female Luer fitting and catheter, thereby sterilizing the female Luer fitting and catheter. The optical plug can transmit light through the optical plug, and can be referred to as a light pipe. The optical plug can also mix various wavelengths of light within the plug, and can be referred to as a light combiner, or light mixer, or light mixing rod. Light from one or multiple light sources can be made more spatially uniform in intensity as it propagates through the optical plug via multiple internal reflections, so that the optical plug can act as a light homogenizer, or light homogenizing rod. Optical plug 300 can have an insertion end 310 and a base end 320. Optical plug 300 can have an intermediate bevel 302 between the insertion end 310 and the base end 320. The insertion end 310 can have a front window 312, an insertion fillet or insertion bevel 314, and an insertion sidewall 316. Insertion sidewall 316 can be frustoconical. The insertion end 310 is designed to be inserted into the internal cavity 212, and can have a corresponding approximately 6% slope. Base end 320 can have a base sidewall 322, base bevel 324, and base window (not shown). Optical plug 300 can be made of fused silica, sapphire (which can be $Al_2O_3$), Teflon, or other material appropriate for the introduction of UV light into the female Luer fitting and indwelling catheter. Appropriate materials can be moldable, formable, or machinable, and with low losses and low absorption in the UV spectrum. The front window 312 and insertion sidewall 316 can be ground to 1500 grit surface finish or other surface finish so as to achieve a desired diffusion effect or other effect. The base window (not shown) and base sidewall 322 can be polished to have a surface quality of 80-50 scratch-dig. The base end of the optical plug can be axisymmetric. The base window (not shown) and base sidewall 322 can be circular or polygonal, so that the cross-section of the base end 320 is in the shape of a circle, or an irregular or regular polygon such as a hexagon. This base end can be a circular prism or other geometric prism. The base sidewall can be polished to a smooth optical surface finish to enable total or near total internal reflection of internal light rays incident on its sidewall surfaces. The polished base sidewall 322 surface can act as a light pipe so that light rays entering the plug through the base window (not shown) are transmitted through the plug to the insertion end 310 via multiple internal reflections off of the base sidewall 322. Multiple light sources can introduce light of different wavelengths into the optical plug, so that the optical plug can act as a light combiner, or light mixer, or light mixing rod. The different wavelengths can be reflected internally within the optical plug and can be combined together. Light from one or multiple light sources can be made more spatially uniform in intensity as it propagates through the optical plug via multiple internal reflections, so that the optical plug can act as a light homogenizer or light homogenizing rod. The cross-section shape of the base sidewall 322 can be designed to achieve desired light-mixing properties. The front window 312 and base window (not shown) can be coated with an anti-reflection (AR) coating to reduce back-reflection of incident light rays. The base sidewall can be designed so that light rays within the base end are transmitted through the length of the base end via multiple internal reflections, thereby allowing the base end to be of arbitrary length.

Figure 3D:
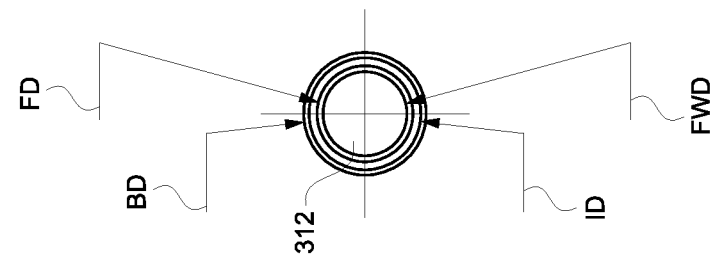
FIG. 3D is an end view of the insertion end of the optical plug of FIG. 3A, according to the embodiment.
Figure 3C:
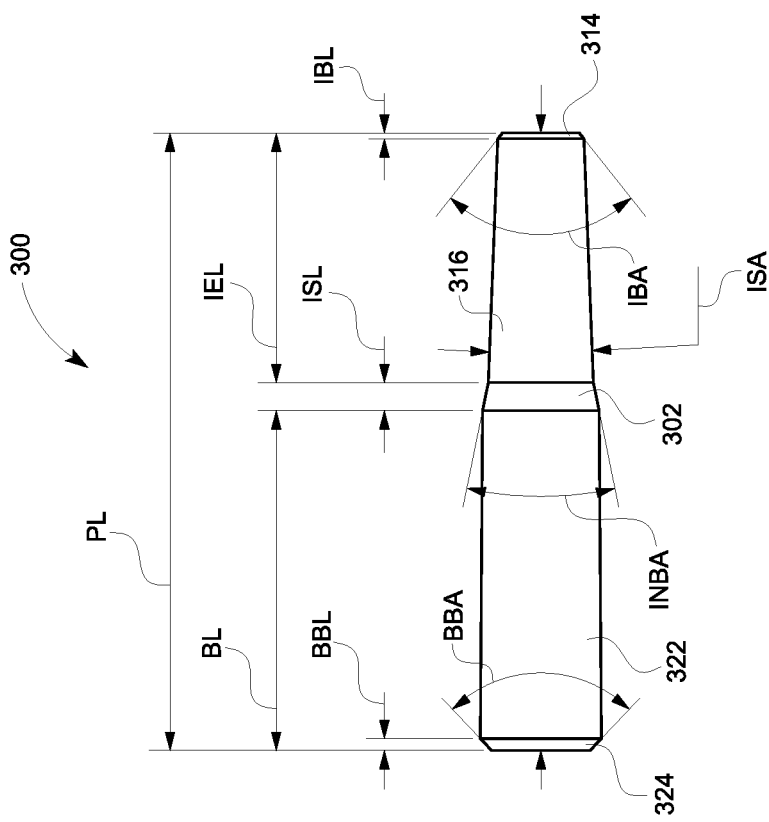
FIG. 3C is a side view of the optical plug of FIG. 3A, according to the embodiment.
Figure 3B:
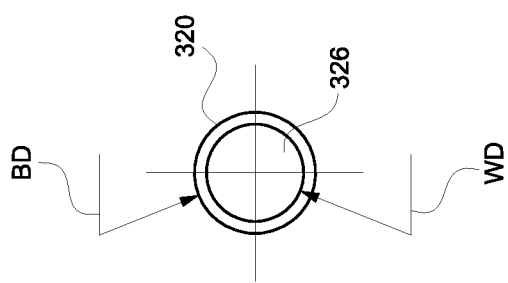
FIG. 3B is an end view of the base end of optical plug of FIG. 3A, according to the embodiment.

FIG. 3B is an end view of the base end of optical plug of FIG. 3A, according to the embodiment. The base window 326 can have a window diameter WD of approximately 4 mm, and the base end 320 can have a base diameter BD of approximately 5 mm. FIG. 3C is a side view of the optical plug of FIG. 3A, according to the embodiment. Optical plug 300 can have a plug length PL of approximately 25.5 mm. Base bevel 324 can have a base bevel length BBL of approximately 0.5 mm, and a base bevel angle BBA of approximately 90°. The base bevel 324 and base sidewall 322 together can have a combined base length BL of approximately 14.2 mm. Intermediate bevel 302 can have an intermediate bevel angle INBA of approximately 22°. Insertion sidewall 316 can have an insertion sidewall length ISL of approximately 10 mm, and an insertion sidewall angle ISA of approximately 3.4°. The insertion bevel 314 can have an insertion bevel length IBL of approximately 0.25 mm, and an insertion bevel angle IBA of approximately 93.4°. The insertion end 310 can have a length IEL of approximately 10.3 mm.

FIG. 3D is an end view of the insertion end of the optical plug of FIG. 3A, according to the embodiment. This end of the optical plug can be inserted into the internal cavity 212 of the Luer fitting, and it is shown here from the perspective from inside the cavity 212. The front window 312 can have a front window diameter FWD of approximately 3.47 mm. The insertion end 310 can have a front diameter FD of approximately 4.0 mm where the sidewall 316 meets the insertion bevel 314. The insertion end 310 can have an intermediate diameter ID of approximately 4.6 mm where the sidewall 316 meets the intermediate bevel 302. The base 320 can have a base diameter BD of approximately 5.0 mm. The optical plug 300 is designed to prevent any shadows or areas of decreased light intensity within the female Luer and indwelling catheter when UV light is introduced through the optical plug 300 and into the female Luer fitting and indwelling catheter. The UV light sterilization treatment of the female Luer fitting and indwelling catheter can be free of shadows.

Figure 4A:
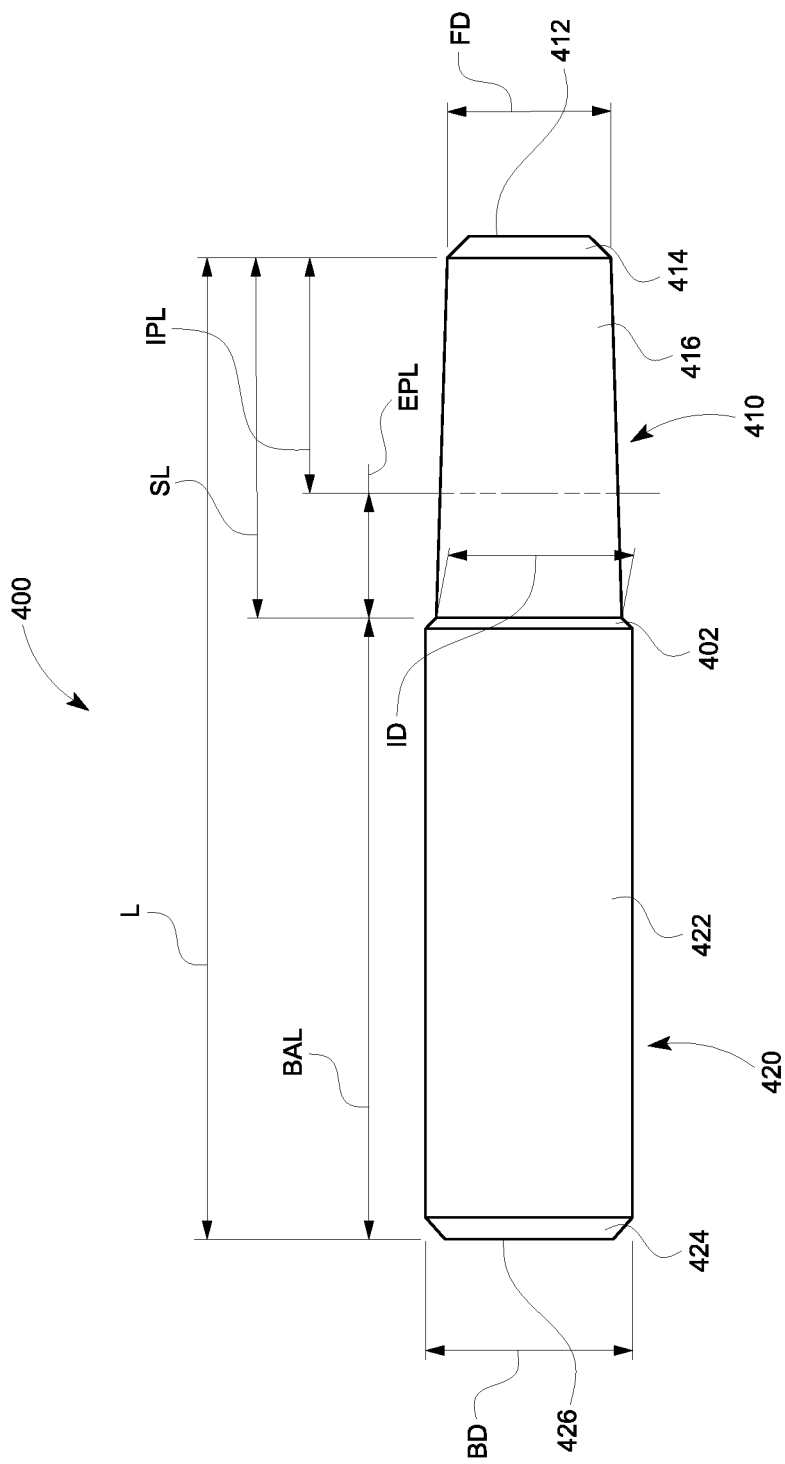
FIG. 4A is side view of an optical plug for use in sterilizing a female Luer fitting and indwelling catheter, according to an alternate embodiment.

FIG. 4A is side view of an optical plug for use in sterilizing a female Luer fitting and indwelling catheter, according to an alternate embodiment. Optical plug 400 is ISO 594 compatible, and can be inserted into an ISO 594 female Luer fitting, allowing UV light to be introduced into a female Luer fitting and catheter, thereby sterilizing the female Luer fitting and catheter. Optical plug 400 can have a length L of 23.63 mm. Optical plug 400 can have an insertion end 410 and a base end 420. Optical plug 400 can have an intermediate bevel 402 between the insertion end 410 and the base end 420. The insertion end 410 can have a front window 412, an insertion bevel 414, and a sidewall 416. Insertion sidewall 416 can be frustoconical. The insertion end 410 is designed to be inserted into the internal cavity 212, and can have a corresponding approximately 6% slope. The insertion end 410 can have a front diameter FD of approximately 3.98 mm where the sidewall 416 meets the insertion bevel 414. The insertion end 410 can have an intermediate diameter ID of approximately 4.50 mm where the sidewall 416 meets the intermediate bevel 402. The sidewall 416 can have a sidewall length SL of approximately 8.63 mm. The insertion portion of the sidewall that is designed to be inserted into the female Luer can have an insertion portion length IPL of approximately 5.63 mm. The external portion of the sidewall that is designed to remain outside of the female Luer can have an external portion length EPL of approximately 3.00 mm. Base end 420 can also have a base sidewall 422, a base bevel 424 and a base window 426. The base bevel 424, base sidewall 422, and intermediate bevel 402 can have a combined base length BAL of approximately 15 mm. The base can have a base diameter BD of approximately 5.00 mm. The base window 426 and base sidewall 422 can be circular or polygonal, so that the cross-section of the base end 420 is in the shape of a circle, or an irregular or regular polygon such as a hexagon. This base end can be a circular prism or other geometric prism. The base sidewall can be polished to a smooth optical surface finish to enable total or near total internal reflection of internal light rays incident on its sidewall surfaces. The polished base sidewall 422 surface can act as a light pipe so that light rays entering the plug through the base window (not shown) are transmitted through the plug to the insertion end 410 via multiple internal reflections off of the base sidewall 422. Multiple light sources can introduce light of different wavelengths into the optical plug, so that the optical plug can act as a light combiner, or light mixer, or light mixing rod. The different wavelengths can then be reflected internally within the optical plug and can be combined together. Light from one or multiple light sources can be made more spatially uniform in intensity as it propagates through the optical plug via multiple internal reflections, so that the optical plug can act as a light homogenizer or light homogenizing rod. The cross-section shape of the base sidewall 422 can be designed to achieve desired light-mixing properties. The front window 412 and base window (not shown) can be coated with an anti-reflection (AR) coating to reduce back-reflection of incident light rays. The base sidewall can be designed so that light rays within the base end are transmitted through the length of the base end via multiple internal reflections, thereby allowing the base end to be of arbitrary length.

Optical plug 400 can be made of a fused silica quartz, sapphire, which can be $Al_2O_3$, or other appropriate materials for allowing UV light to pass into the base window 426, through the optical plug 400, and into the female Luer and indwelling catheter. The insertion end 410, insertion bevel 414, and the front window 412 can be ground to a 1500 grit. The base end 420, base sidewall 422, and base window 426 can be polished to have a surface quality of 50-80 scratch-dig. The optical plug 400 is designed to prevent any shadows or areas of decreased light intensity within the female Luer and indwelling catheter when UV light is introduced through the optical plug 400 and into the female Luer fitting and indwelling catheter. The UV light sterilization treatment of the female Luer and indwelling catheter can be free of shadows.

Figure 4B:
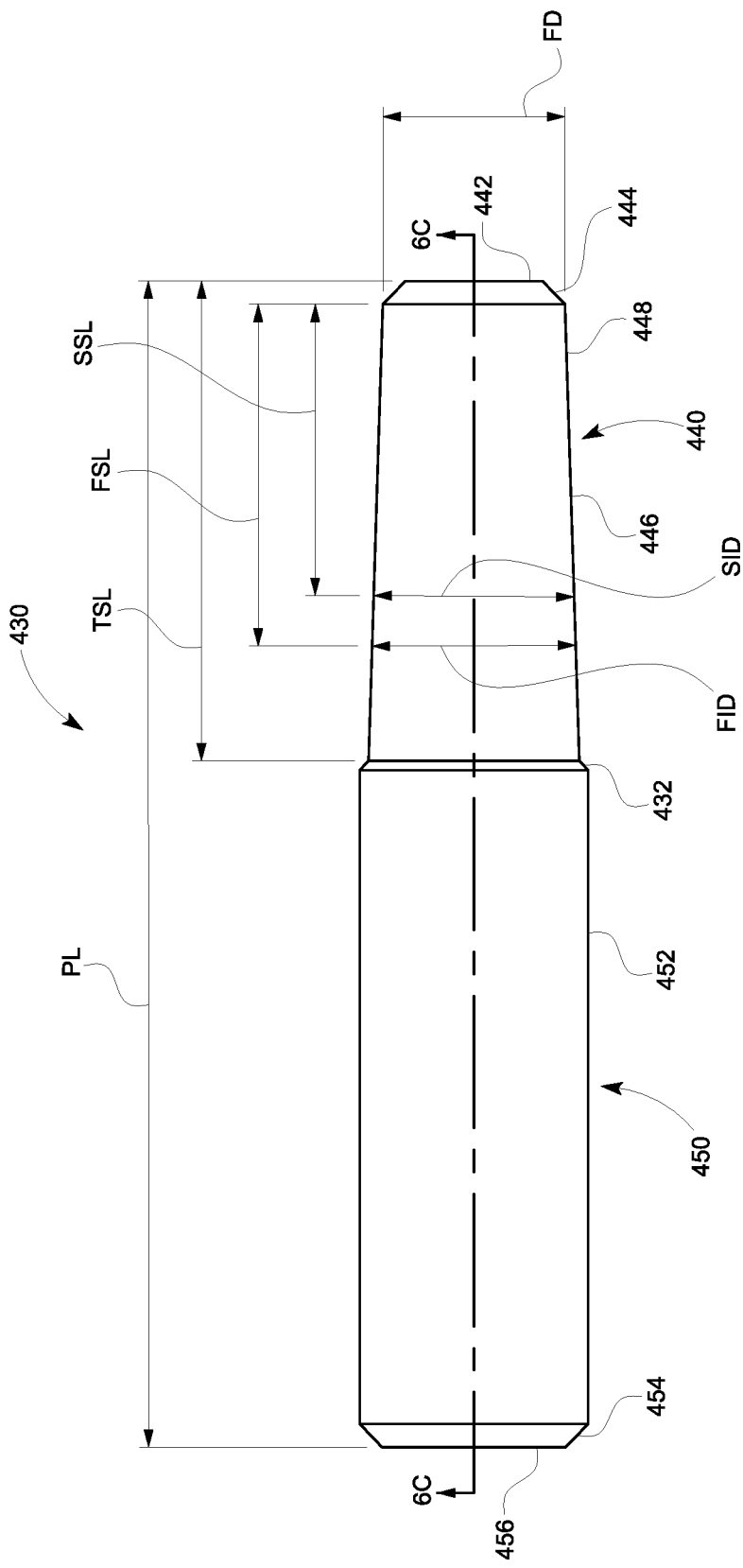
FIG. 4B is a side view of an optical plug according to an alternate embodiment.

FIG. 4B is a side view of an optical plug according to an alternate embodiment. Optical plug 430 is ISO 594 compatible, and can be inserted into an ISO 594 female Luer fitting, allowing UV light to be introduced into a female Luer fitting and catheter, thereby sterilizing the female Luer fitting and catheter. Optical plug 430 can have an insertion end 440 and a base end 450. Optical plug 430 can have an intermediate bevel 432 between the insertion end 440 and the base end 450. The insertion end 440 can have a front window 442, an insertion bevel 444, and a sidewall 446. Insertion sidewall 446 can be frustoconical. The insertion end 440 can have an insertion portion 448 that is designed to be inserted into the internal cavity 212. The insertion portion 448 can have an approximately 6% slope corresponding to the female Luer fitting. Base end 450 can also have a base sidewall 452, base bevel 454, and base window 456. The base window 456 and base sidewall 452 can be circular or polygonal, so that the cross-section of the base end 450 is in the shape of a circle, or an irregular or regular polygon such as a hexagon. This base end can be a circular prism or other geometric prism. The base sidewall can be polished to a smooth optical surface finish to enable total or near total internal reflection of internal light rays incident on its sidewall surfaces. The polished base sidewall 452 surface can act as a light pipe so that light rays entering the plug through the base window (not shown) are transmitted through the plug to the insertion end 440 via multiple internal reflections off of the base sidewall 452. Multiple light sources can introduce light of different wavelengths into the optical plug, so that the optical plug can act as a light combiner, or light mixer, or light mixing rod. The different wavelengths can then be reflected internally within the optical plug and can be combined together. Light from one or multiple light sources can be made more spatially uniform in intensity as it propagates through the optical plug via multiple internal reflections, so that the optical plug can act as a light homogenizer or light homogenizing rod. The cross-section shape of the base sidewall 452 can be designed to achieve desired light-mixing properties. The front window 442 and base window (not shown) can be coated with an anti-reflection (AR) coating to reduce back-reflection of incident light rays. The base sidewall can be designed so that light rays within the base end are transmitted through the length of the base end via multiple internal reflections, thereby allowing the base end to be of arbitrary length.

Optical plug 430 can be made of a fused silica, sapphire (which can be $Al_2O_3$), or other material appropriate for the introduction of UV light into the female Luer fitting and indwelling catheter. By way of non-limiting example, the optical plug can be made of a GE type 214 fused silica rod or the equivalent. The front window 442 and insertion portion 448 can be ground to approximately 1500 grit. The base window can be polished to have a surface quality of 80-50 scratch-dig.

Optical plug 430 can have a plug length PL of approximately 25.5 mm. Insertion end 440 can have a front diameter FD where the sidewall 446 meets the insertion bevel 444 of approximately between 3.99 mm and 3.925 mm. The insertion end can have a total insertion sidewall length TSL of approximately 10.5 mm. The insertion end can have a first insertion sidewall length FSL of approximately 7.5 mm, and can have a first insertion diameter FID at the first insertion sidewall length FSL of approximately between 4.4 mm and 4.375 mm. The insertion end can have a second insertion sidewall length SSL of approximately 6.42 mm, and a second insertion diameter SID at the second insertion sidewall length SSL of approximately between 4.375 mm and 4.31 mm. The portion of the insertion end 440 between the first insertion diameter and the front diameter can have an approximately 6% slope. These dimensions are designed to approximately correspond with the dimensions of the female Luer fitting 210, so that the insertion portion 448 of the optical plug 430 can be inserted into the female Luer fitting 210.

Figure 5:
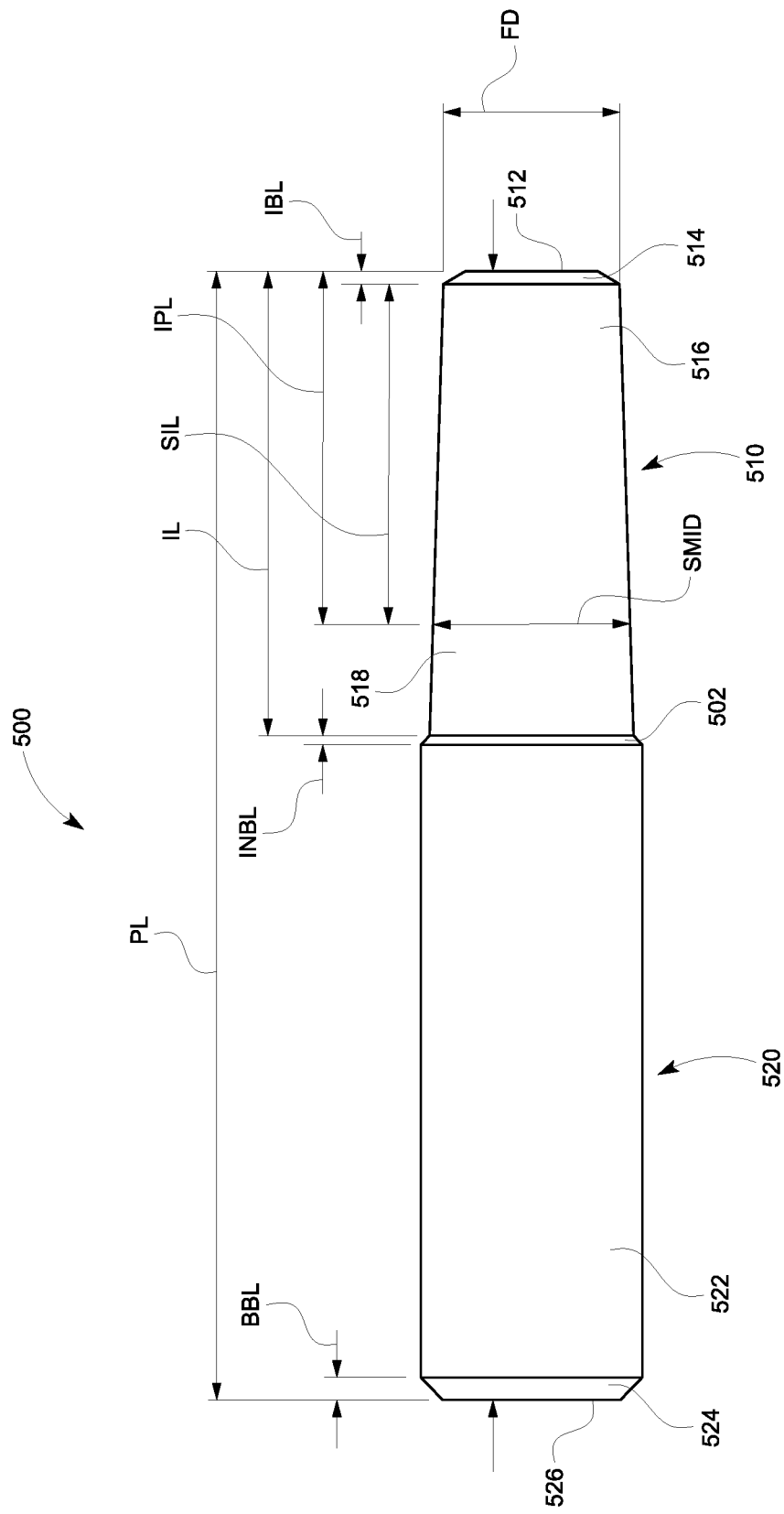
FIG. 5 is a side view of an optical plug according to an alternate embodiment.

FIG. 5 is a side view of an optical plug according to an alternate embodiment. Optical plug 500 is ISO 594 compatible, and can be inserted into an ISO 594 female Luer fitting, allowing UV light to be introduced into a female Luer fitting and catheter, thereby sterilizing the female Luer fitting and catheter. Optical plug 500 can have an insertion end 510 and a base end 520. Optical plug 500 can have an intermediate bevel 502 between the insertion end 510 and the base end 520. The insertion end 510 can have a front window 512, an insertion bevel 514, and an insertion sidewall 516. Insertion sidewall 516 can be frustoconical. The insertion end 510 can have an insertion portion 518 that is designed to be inserted into the internal cavity 212. The insertion portion 518 can have an approximately 6% slope corresponding to the female Luer fitting. Base end 520 can also have a base sidewall 522, base bevel 524, and base window 526. The base window 526 and base sidewall 522 can be circular or polygonal, so that the cross-section of the base end 520 is in the shape of a circle, or an irregular or regular polygon such as a hexagon. This base end can be a circular prism or other geometric prism. The base sidewall can be polished to a smooth optical surface finish to enable total or near total internal reflection of internal light rays incident on its sidewall surfaces. The polished base sidewall 522 surface can act as a light pipe so that light rays entering the plug through the base window 526 are transmitted through the plug to the insertion end 510 via multiple internal reflections off of the base sidewall 522. Multiple light sources can introduce light of different wavelengths into the optical plug, so that the optical plug can act as a light combiner, or light mixer, or light mixing rod. The different wavelengths can then be reflected internally within the optical plug and can be combined together. Light from one or multiple light sources can be made more spatially uniform in intensity as it propagates through the optical plug via multiple internal reflections, so that the optical plug can act as a light homogenizer or light homogenizing rod. The cross-section shape of the base sidewall 522 can be designed to achieve desired light-mixing properties. The front window 512 and base window 526 can be coated with an anti-reflection (AR) coating to reduce back-reflection of incident light rays. The base sidewall can be designed so that light rays within the base end are transmitted through the length of the base end via multiple internal reflections, thereby allowing the base end to be of arbitrary length.

Optical plug 500 can be made of a fused silica, sapphire (which can be $Al_2O_3$), or other material appropriate for the introduction of UV light into the female Luer fitting and indwelling catheter. The front window 512 and insertion portion 518 can be ground to approximately 1500 grit. The base window can be polished to have a surface quality of 80-50 scratch-dig.

Insertion end 510 can have a front diameter FD where the sidewall 516 meets the insertion bevel 514 of approximately between 3.99 mm and 3.925 mm. The sidewall can have a maximum insertion diameter SMID of approximately between 4.44 mm and 4.375. The sidewall can have a sidewall insertion length SIL of approximately 7.5 mm. The portion of the insertion end 510 between the maximum insertion diameter and the front diameter can have an approximately 6% slope. The portion of the insertion end 510 from the maximum insertion diameter SMID to the front window 512 is the insertion portion 518. These dimensions are designed to approximately correspond with the dimensions of the female Luer fitting 210, so that the insertion portion 518 of the optical plug 500 can be inserted into the female Luer fitting 210 up to the maximum insertion diameter SMID.

Insertion bevel 514 can have an insertion bevel length IBL of approximately 0.25 mm+/−0.125 mm. Insertion end can have an insertion portion length IPL of 7.75 mm. Insertion end 510 can have an insertion end length IL of approximately 10.3 mm. Optical plug 500 can have a plug length PL of approximately 25.5 mm. Base bevel 524 can have a base bevel length BBL of approximately 0.5 mm or less. Intermediate bevel 502 can have an intermediate bevel length INBL of approximately 1 mm or less.

The dimensions provided herein are intended as non-limiting examples of optical plugs that are appropriate for insertion within and sterilization of an ISO 594 female Luer lock. Variations in dimensions may be necessary, for example, when a protective cover, made of plastic or other UV optically transmissive materials, is used over the optical plug. By way of non-limiting example, the insertion end may have a diameter that is 25 to 150 um smaller, depending on the thickness of a UV-transmissive cover. If a protective plastic cover is used over the optical plug, the optical plug dimensions will need to be reduced by an amount approximately corresponding to the thickness of the protective cover. Furthermore, variations on these exemplary dimensions are possible for alternate connector types.

The optical plug 500 is designed to prevent any shadows or areas of decreased light intensity within the female Luer and indwelling catheter when UV light is introduced through the optical plug 500 and into the female Luer fitting and indwelling catheter. The UV light sterilization treatment of the female Luer fitting and indwelling catheter can be free of shadows.

Figure 6A:
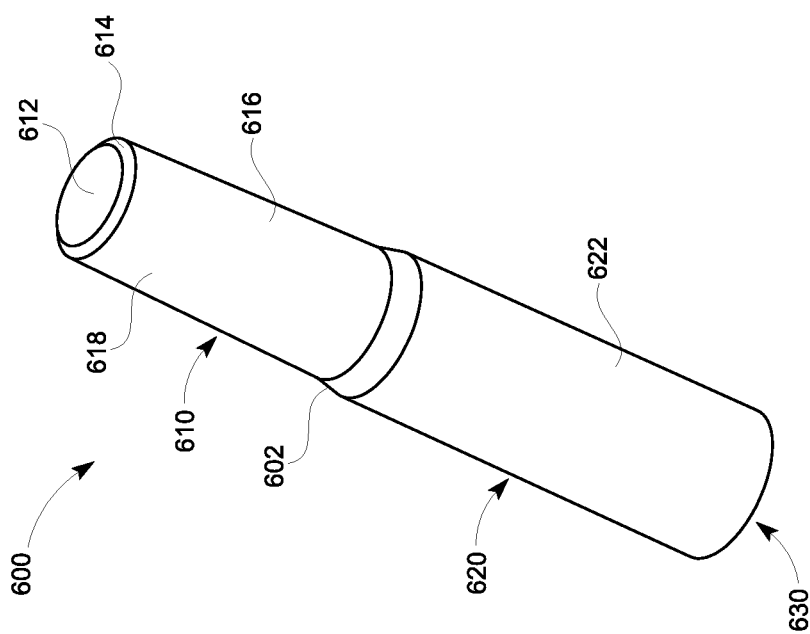
FIG. 6A is a perspective view of an exemplary cover for an optical plug, according to an embodiment.

FIG. 6A is a perspective view of an exemplary cover for an optical plug, according to an embodiment. The cover is UV-transmissive, and can be disposable. The cover 600 can have an insertion end 610 and a base end 620. The cover 600 can have an intermediate bevel 602 between the insertion end 610 and the base end 620. The insertion end can have a front window 612, an insertion bevel 614, and an insertion sidewall 616. Insertion sidewall 616 can be frustoconical. The insertion end 610 can have an insertion portion 618 that is designed to be inserted into the internal cavity 212. The insertion portion 618 can have an approximately 6% slope corresponding to the female Luer fitting. Base end 620 can have a base sidewall 622, and a rear opening 630. An optical plug can be inserted into the protective cover 600 through the rear opening 630.

The cover 600 can be made of a UV-transmissive material such as a disposable plastic. By way of non-limiting example, the cover can be made of a fluoropolymer, such as fluorinated ethylene propylene (FEP), ethylene-tetrafluoroethylene (ETFE), or polyvinylidene fluoride (PVDF) because of the transmissive properties of these materials for UV light. The cover 600 can have an exemplary thickness in a range of 0.001 to 0.005 inch (0.0254 to 0.127 mm), and preferably in a range of 0.0001 to 0.0002 inch. The cover 600 is sized and shaped to be placed over an optical plug, and be inserted into a female Luer fitting with the optical plug inside. The exterior dimensions of the cover 600 can be approximately the same as the exterior dimensions of any of the above exemplary optical plugs. The cover 600 can have appropriate exterior dimensions to meet the ISO 594 specification and can be inserted into the female Luer lock. An optical plug that is designed for use with a cover can have dimensions that are reduced by approximately the thickness of the cover.

Light can enter the optical plug through the base window of the optical plug. The cover 600 may not cover the base window of the optical plug. Light can then travel through the optical plug, and different wavelengths can be combined through internal reflection in the optical plug. The light can then exit the insertion sidewall, insertion bevel, and front window of the optical plug. The light can then pass through the insertion sidewall 616, insertion bevel 614, and front window 612 of the cover. Light can pass through the cover into the female Luer fitting and the attached catheter.

Various embodiments of the cover can sheathe all of the optical plug, most of the optical plug, or various amounts of the optical plug. The cover can sheathe the front window plus various amounts of the optical plug. In some embodiments, the cover can sheathe the front window plus at least a portion of the insertion end of the optical plug. In some embodiments of the cover, the base end of the optical plug may not be sheathed by the cover. In some embodiments, a portion of the insertion end of the optical plug may not be sheathed by the cover.

Figure 6C:
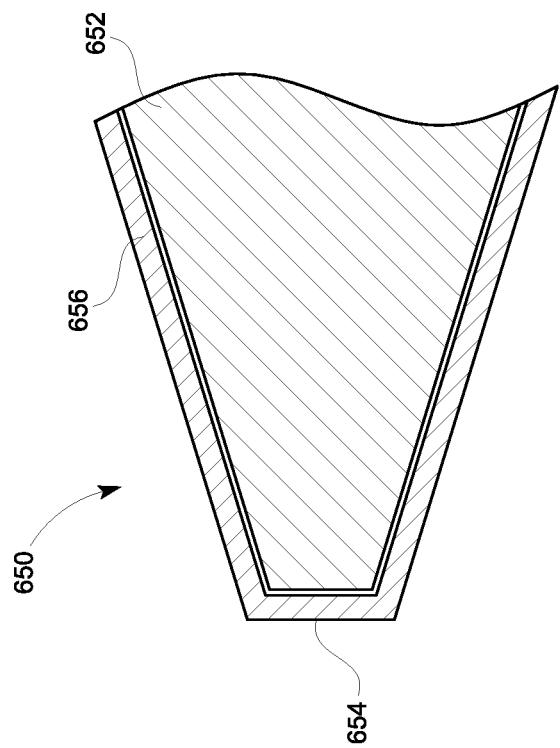
FIG. 6C is a cross section view of an exemplary cover for an optical plug along cross section line 6C-6C of FIG. 4B, according to an embodiment.
Figure 6B:
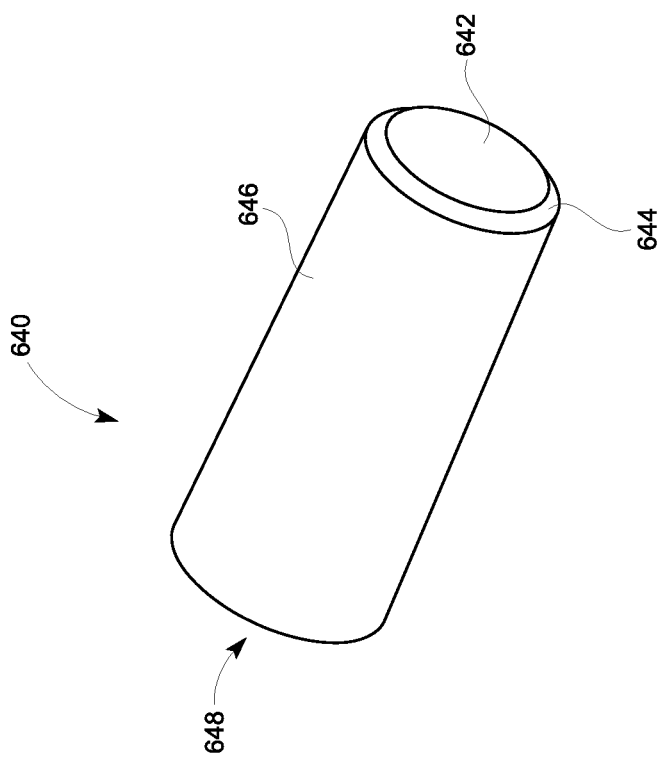
FIG. 6B is a perspective view of an exemplary cover for an optical plug, according to an embodiment.

FIG. 6B is a perspective view of an exemplary cover for an optical plug, according to a different embodiment. The cover is UV-transmissive, and can be disposable. The cover 640 can sheathe all or a portion of the insertion end of an optical plug. The cover 640 can have a front window 642, a bevel 644, and a sidewall 646. Sidewall 646 can be frustoconical. The cover 640 can be designed to sheathe at least a portion of the insertion end of an optical plug, and to be inserted into the internal cavity 212 of a female Luer lock. The sidewall 646 can have an approximately 6% slope corresponding to the female Luer fitting. The cover 640 can have a rear opening 648. An optical plug can be inserted into the cover 640 through the rear opening 648.

The cover 640 can be made of a UV-transmissive material such as a disposable plastic. The cover 640 can have an exemplary thickness in a range of 0.001 to 0.005 inch (0.0254 to 0.127 mm), and preferably in a range of 0.0001 to 0.0002 inch. The cover 640 is sized and shaped to be placed over an optical plug, and be inserted into a female Luer fitting with the optical plug inside. The exterior dimensions of the cover 640 can be approximately the same as the exterior dimensions of the insertion end of any of the above exemplary optical plugs. The cover 640 can have appropriate exterior dimensions to meet the ISO 594 specification and can be inserted into the female Luer lock. An optical plug that is designed for use with a cover can have dimensions that are reduced by approximately the thickness of the cover.

Light can enter the optical plug through the base window of the optical plug. The cover 640 may not cover the base window of the optical plug. Light can then travel through the optical plug, and different wavelengths can be combined through internal reflection in the optical plug. The light can then exit the insertion sidewall, insertion bevel, and front window of the optical plug. The light can then pass through the sidewall 646, bevel 644, and front window 642 of the cover. Light can pass through the cover into the female Luer fitting and the attached catheter. In some embodiments, the cover may be free of an insertion bevel. In some embodiments, the cover can have a curved exterior, or curved edges between the front window and the sidewall.

FIG. 6C is a cross section view of an exemplary cover for an optical plug along cross section line 6C-6C of FIG. 4B, according to an embodiment. Cover 650 is shown covering an optical plug 652. Cover 650 can be free of a front bevel, and can have a front window 654 and a sidewall 656. Sidewall 656 can be frustoconical. The cover 650 can be designed to sheathe at least a portion of the insertion end of an optical plug, and to be inserted into the internal cavity 212 of a female Luer lock. The sidewall 656 can have an approximately 6% slope corresponding to the female Luer fitting. The cover 650 can have a rear opening (not shown). An optical plug can be inserted into the cover 650 through the rear opening.

The cover 650 can be made of a UV-transmissive material such as plastic. The cover 650 can have an exemplary thickness in a range of 0.001 to 0.005 inch (0.0254 to 0.127 mm), and preferably in a range of 0.0001 to 0.0002 inch. The cover 650 is sized and shaped to be placed over an optical plug, and be inserted into a female Luer fitting with the optical plug inside. The exterior dimensions of the cover 650 can be approximately the same as the exterior dimensions of the insertion end of any of the above exemplary optical plugs. The cover 650 can have appropriate exterior dimensions to meet the ISO 594 specification and can be inserted into the female Luer lock. An optical plug that is designed for use with a cover can have dimensions that are reduced by approximately the thickness of the cover.

Light can enter the optical plug through the base window of the optical plug. The cover 650 may not cover the base window of the optical plug. Light can then travel through the optical plug, and different wavelengths can be combined through internal reflection in the optical plug. The light can then exit the sidewall and front window of the optical plug. The light can then pass through the sidewall 656 and front window 654 of the cover. Light can pass through the cover into the female Luer fitting and the attached catheter. The cover can have a curved exterior, or curved edges between the front window and the sidewall.

Figure 7:
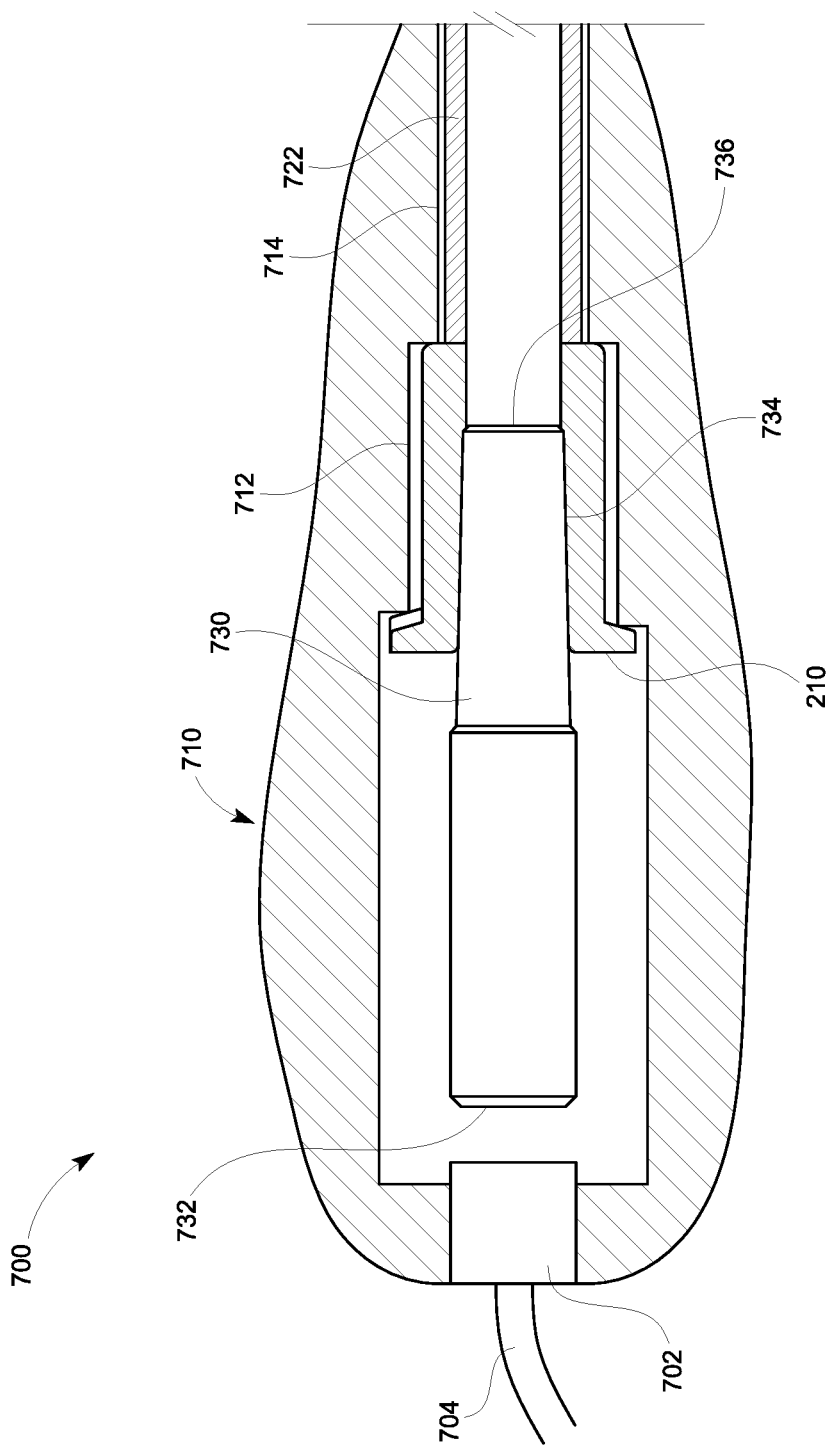
FIG. 7 is a cross section view of an exemplary UV sterilizer for sterilizing a female Luer fitting and catheter, according to an embodiment.

FIG. 7 is a cross section view of an exemplary UV sterilizer for sterilizing a female Luer fitting and catheter. Sterilizer 700 can have a UV light unit 702 and a cord 704. UV light unit 702 can include at least one UV LED, or other source of UV light. Cord 704 can connect to a power source, external control system, or both. Sterilizer 700 can have a body 710. UV light unit 702 can also receive power from an internal battery (not shown). Various electronic components (not shown) can condition and/or convert and distribute electrical power to the electrical and/or optoelectrical components such as UV light unit 702. These electronic components can be within the sterilizer body or can be located within a base unit connected to the sterilizer by cord 704. The sterilizer can include a means of controlling and/or adjusting the light output of the at least one UV light source, wherein the light output of the at least one UV light source is measured and then adjusted accordingly to maintain a desired light output level. The sterilizer body 710 can be used to hold the female Luer fitting 210 and the catheter 722. The sterilizer body 710 can have a female Luer fitting harness 712 to hold the female Luer fitting 210 in a straight line extending outward from the UV light unit 702. Body 710 can have a catheter harness 714 designed to hold the catheter 722 in a straight line extending outward from the UV light unit 702. Catheter harness 714 can be at least 6 cm long. Catheter harness 714 prevents shadows by keeping the catheter straight, thereby allowing the UV light to irradiate the catheter without any shadows. Catheter harness 714 can align the catheter and female Luer fitting with the optical axis of the sterilizer. This can be accomplished by holding the soft, flexible catheter in a straightened orientation so that there are no bends in the catheter, while also securing the catheter in a coaxial position with respect to the principal center axis of the optical plug. Catheter harness 714 additionally prevents ambient light from reaching the lumen of the catheter 722 so that photoreactivation of microorganisms within the catheter lumen is prevented. Female Luer fitting harness 712 additionally prevents ambient light from reaching the lumen of the female Luer fitting 210 so that photoreactivation of microorganisms within the lumen of the female Luer fitting 210 is prevented. Ambient light is prevented from illuminating the catheter and the female Luer fitting because ambient light enables microorganisms to repair DNA damage.

A user can insert the insertion end of an optical plug 730 into a female Luer fitting 210 with an attached catheter 722. A user can optionally include a UV-transparent cover 600 over the optical plug 730 before inserting the optical plug 730 into the female Luer fitting 210. The UV-transparent cover 600 can be disposable. This cover can have a thickness in a range of 0.001 to 0.005 inch (0.0254 to 0.127 mm), and preferably in a range of 0.0001 to 0.0002 inch. It should be clear that the dimensions of the insertion end of the optical plug will need to be decreased to account for the thickness of the transparent cover, so that the optical plug and cover together meet the ISO 594 spec and can be inserted into the female Luer lock. The optical plug and optional UV-transparent cover are designed to work together to meet ISO 594 requirements. An optical plug that is designed for use with a UV-transparent cover may not be used without the UV-transparent cover, because the optical plug with decreased dimensions that is designed to be used with a cover will not meet the ISO 594 requirements without the associated UV-transparent cover. The UV-transparent cover can be a semi-rigid plastic polymer shape that can slip over the insertion end of the optical plug. In various embodiments the cover can be made of polymers in the fluoropolymer family, including FEP, PTFE, etc. The cover can be manufactured using a compression molding process. The interior surface of the cover can be coated with an impedance matching film or other anti-reflection film that can reduce back-reflection. This film, which can be an oil or other material, can reduce power loss by reducing back-reflection at the material interface between the plug and the cover.

The user can then place the catheter 722, optional protective cover, and the female Luer fitting 210 with the inserted optical plug 730 into the body 710 of the sterilizer 700. The catheter 722 can be placed within the catheter harness 714. The female Luer fitting can be placed within the female Luer fitting harness 712. The sterilizer 700 can then be closed around the catheter 722, female Luer fitting 210 and optical plug 730. The sterilizer body 710 can prevent non-UV light from entering into the sterilizer 700. The UV light unit 702 can be switched on, so that UV light radiates outward from the UV light unit 702 and into the base window 732 of the optical plug 730. The UV light can then radiate through the optical plug 730. UV light can radiate out of the sidewall 734 and front window 736 of the optical plug, thereby irradiating the inner surfaces of the female Luer fitting 210 and the inside of the catheter 722. The catheter harness 714 holds the catheter in a straight line extending outward from the UV light unit 702 so that UV light radiates the inner surfaces of the female Luer fitting 210 and the inside of the catheter 722 without shadows or areas of decreased light intensity. Sterilizer 700 can kill pathogenic microbes dwelling intraluminally inside the catheter surface.

The UV light unit 702 can provide light in a range of wavelengths, including wavelengths outside of the UV spectrum. Light can be provided in desired wavelengths ranging from approximately 100 nm to 700 nm. The UV light unit 702 can provide UV-C light in a range of approximately 250 nm to 280 nm, and preferably in a range of approximately 260 nm to 270 nm. The UV light unit 702 can also provide UV-A light in a range of approximately 315 nm to 400 nm. The combination of UV-A and UV-C light together can have a synergistic sterilizing effect, so that the sterilizing effect of the two light wavelengths together can be greater than the sum of each light wavelength individually.

Figure 8:
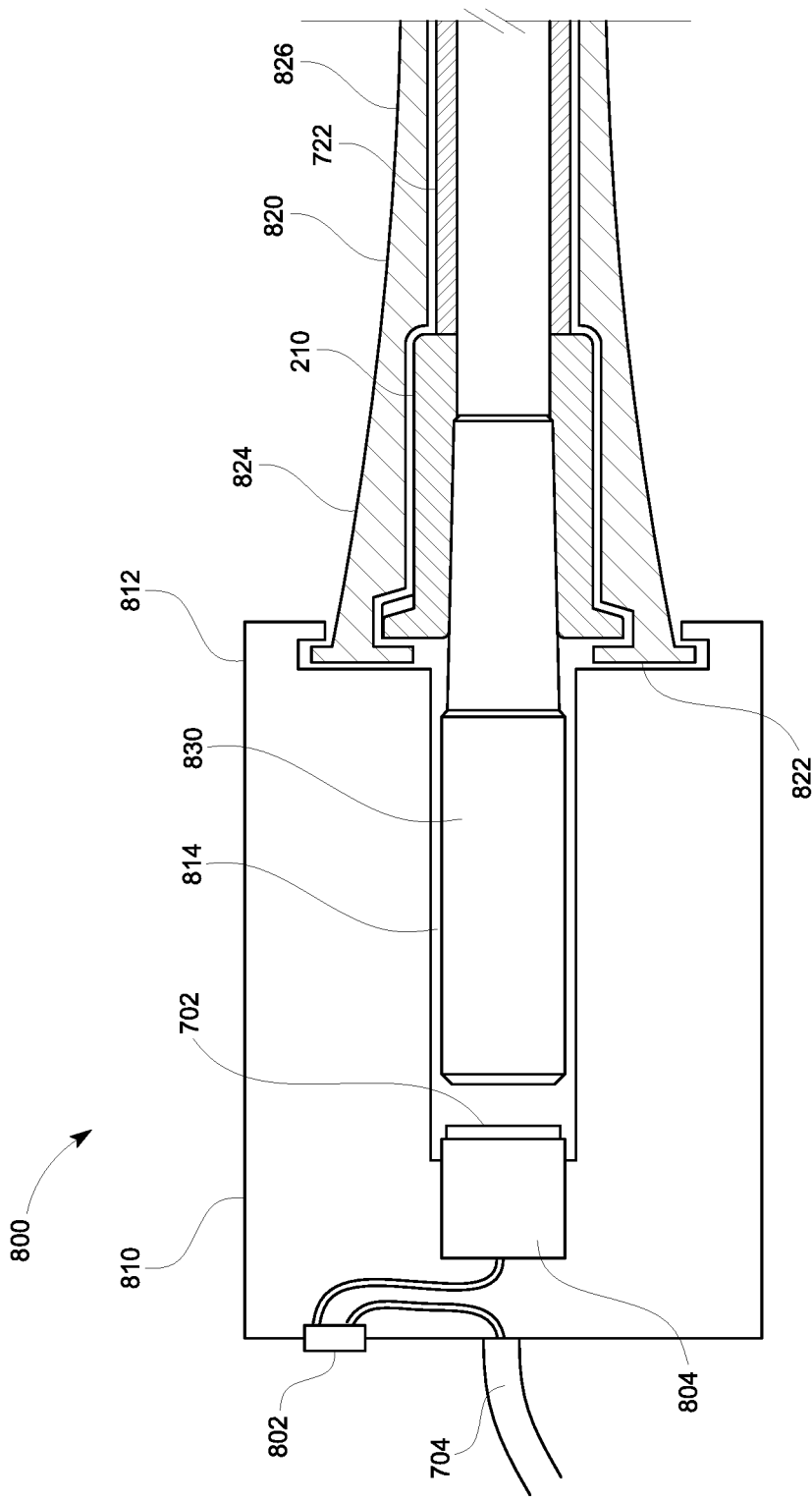
FIG. 8 is a cross section view of an exemplary UV sterilizer for a female Luer fitting and catheter, according to an alternate embodiment.

FIG. 8 is a cross section view of an exemplary UV sterilizer for a female Luer fitting and catheter, according to an alternate embodiment. Sterilizer 800 can have a sterilizer body 810, a catheter harness 820, and an optical plug 830. The sterilizer body 810 can have a harness-engaging region 812. The harness engaging region 812 can engage with the catheter harness 820. The harness engaging region 812 and the catheter harness 820 can be engaged through threadings, or the sterilizer body can be constructed as a two-piece clamshell that can be closed around the catheter harness 820, or other possible arrangements. The sterilizer body 810 can have an optical plug region 814 that optionally can be in contact with the optical plug 830 to ensure proper alignment of the optical plug 830 with the central axis of the sterilizer 800. The optical plug region can optionally have a reflective coating so that any light that escapes from the base end of the optical plug due to scratches or other damage to the base end can be redirected back into the optical plug so that it can irradiate the inside of the female Luer fitting 210 and attached catheter 722.

The sterilizer body 810 can have a UV light unit 702 and a cord 704. UV light unit 702 can include at least one UV LED, or other source of UV light. Cord 704 can connect to an external power source, external control system, electrical control unit, and/or external user interface. Sterilizer 800 can have can have a user interface 802. User interface 802 can include a means for controlling and/or adjusting the light output of the at least one UV light source. Sterilizer 800 can have an electrical control unit 804. Electrical control unit 804 can condition, convert, and/or distribute electrical power to UV light 702. Power and/or external controls can be carried through cord 704 to user interface 802 and to electrical control unit 804, and from electrical control unit 804 to UV light unit 702. In various embodiments, components such as the user interface 802 and electrical control unit 804 can be within the sterilizer body or in an external base unit, and connections between them can be configured appropriately.

Catheter harness 820 can have a sterilizer body engagement feature 822, such as threads, tabs, or other possible arrangements configured to engage with the sterilizer body 810. Catheter harness 820 can be configured to secure and align the catheter 722 and female Luer fitting 210 with the optical axis of the sterilizer. Catheter harness 820 can have a Luer-holding region 824 and a catheter-holding region 826. In an embodiment, Luer-holding region 824 can engage with the threads of the female Luer fitting 210, or can be a two-piece clamshell arrangement that holds the female Luer lock in place, or other configurations. Catheter-holding region 826 can hold and align the catheter 722 in a straightened orientation so that there are no bends in the catheter, while also securing the catheter in a coaxial position with respect to the principal center axis of the optical plug. The catheter-holding region 826 can be at least 6 cm long, and can prevent shadows in the first 6 cm of the catheter 722 so that UV light can irradiate at least the first 6 cm of the catheter 722 without (free of) any shadows. Catheter harness 820 additionally prevents ambient light from reaching the lumen of the catheter 722 so that photoreactivation of microorganisms within the catheter lumen is prevented. Catheter harness 820 additionally prevents ambient light from reaching the lumen of the female Luer fitting 210 so that photoreactivation of microorganisms within the lumen of the female Luer fitting 210 is prevented.

A user can insert an optical plug 830 into a female Luer fitting 210 with an attached catheter 722. If the optical plug is designed for use with a UV-transparent cover, a user can include a UV-transparent cover 600 over the optical plug 830 before inserting the optical plug 830 into the female Luer fitting 210. The user can then secure the female Luer fitting 210 and attached catheter 722 within the catheter harness 820. The catheter harness 820 can then be secured within the sterilizer body 810. The user can use user interface 802 to send power to the UV light unit 702, thereby causing UV light to shine into the rear window of the optical plug 830, through the body of the optical plug, and out of the insertion end where it can irradiate the inside of the female Luer lock and the attached catheter. This irradiation can kill many bacteria and other microbes present within the female Luer lock and attached catheter without (free of) the use of chemicals or drugs such as antibiotics or antimocrobials. Because prolonged high doses of UV-C exposure can damage DNA in human cells and can be a carcinogen, the sterilizer 800 can be designed to prevent or minimize leakage of light from the sterilizer.

FIG. 9 is a schematic block diagram of exemplary components of a sterilizer, according to an embodiment. Sterilizer 900 can have a user interface 902, a power conditioning and distribution module 904, a UV light source control module 906, a UV light source 908, and an optical plug 910 with insertion end 912 (not shown to scale). A user can use the user interface 902 to control the sterilizer 900. The sterilizer can also include a user interface for an operator to adjust sterilizer settings and be informed of sterilizer operational and functional status. The user interface can consist of buttons, knobs, switches, touch-sensitive surfaces, display screens, and/or touchscreens, etc. UV light source 908 can then emit light into the optical plug 910, and the light can be emitted out of the insertion end 912. Sterilizer 900 can engineer the light structure, including the duty cycle and pulse frequency.

A user can use the user interface to control the time duration of UV irradiation. Longer irradiation times can result in greater germicidal efficacy. A user can use additional irradiation durations if, for example, a treatment has been skipped, or if the user suspects greater contamination than normal, or the user otherwise wants to increase germicidal efficacy. A user can use the user interface to control the radiant power of UV irradiation. Higher radiant power can result in greater germicidal efficacy. A user can use the user interface to control the proportion of time duration and/or radiant power at different wavelengths, e.g. 40% UV-A and 60% UV-C. Different organisms can be more or less susceptible to different wavelengths, so the radiant power and/or time duration of different wavelengths can be engineered for killing a specific organism. A user can use the user interface to control the duty cycle and/or pulse frequency. A user can control the duty cycle and/or pulse frequency to target a specific organism. A user can use the user interface to perform a manual calibration, status check, and or manual self-test of the sterilizer.

Figure 10:
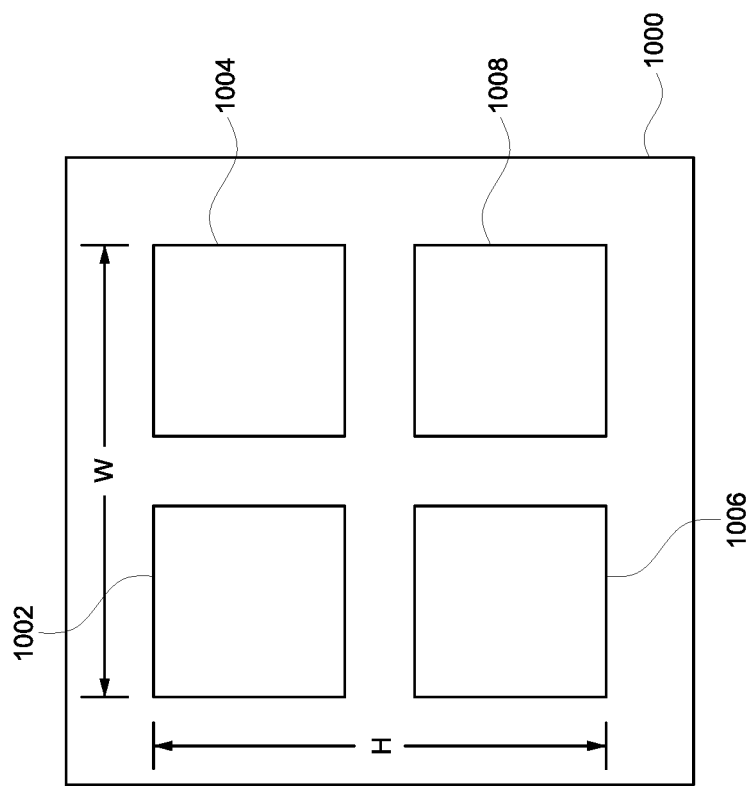
FIG. 10 is a diagram of an exemplary UV light source unit, according to an embodiment.

FIG. 10 is a diagram of an exemplary UV light source unit, according to an embodiment. UV light source unit 1000 can have a multitude of LEDs arranged in an LED array. As shown, UV light source unit 1000 can have LEDs 1002, 1004, 1006, and 1008. LEDs 1002, 1004, 1006, and 1008 can be all the same wavelength, all different wavelengths, or a combination of possible wavelengths. A diagonal distance from one outer corner of the LED array to the opposite outer corner the LED array, defined as the square root of $(W^2+H^2)$, can be equal to or less than the diameter of the base end of the optical plug. The diagonal distance can be equal to or less than the diameter of the base window. Light from the UV light source 1000 can be directed from the LEDs into the base end of the optical plug.

Figure 11:
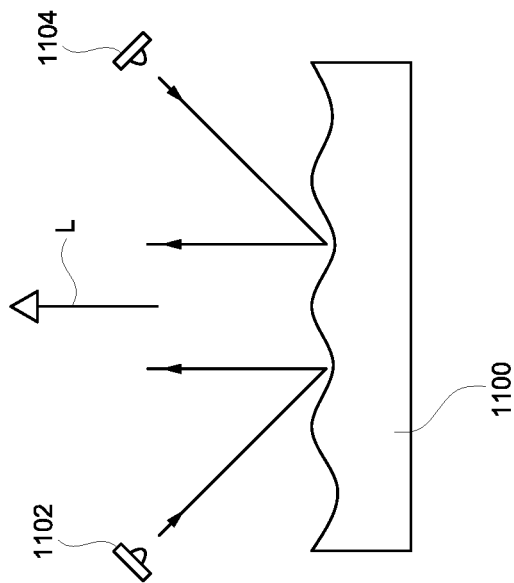
FIG. 11 shows a light beam redirector, according to an embodiment.

FIG. 11 shows a light beam redirector, according to an embodiment. The light beam redirector 1100 can be a component in the UV light unit 702. A UV-C light source 1102, such as an LED, can be focused on the light beam redirector 1100 so that the light is directed out of the UV light unit 702 along the direction of light vector L and towards the optical plug 730. A UV-A light source 1104, such as an LED, can be focused on the light beam redirector 1100 so that the light is directed out of the UV light unit 702 along the direction of light vector L and towards the optical plug 730. UV-C and UV-A radiation can be emitted from the UV light unit 702 simultaneously, individually, or in various engineered forms of pulses.

Figure 12:
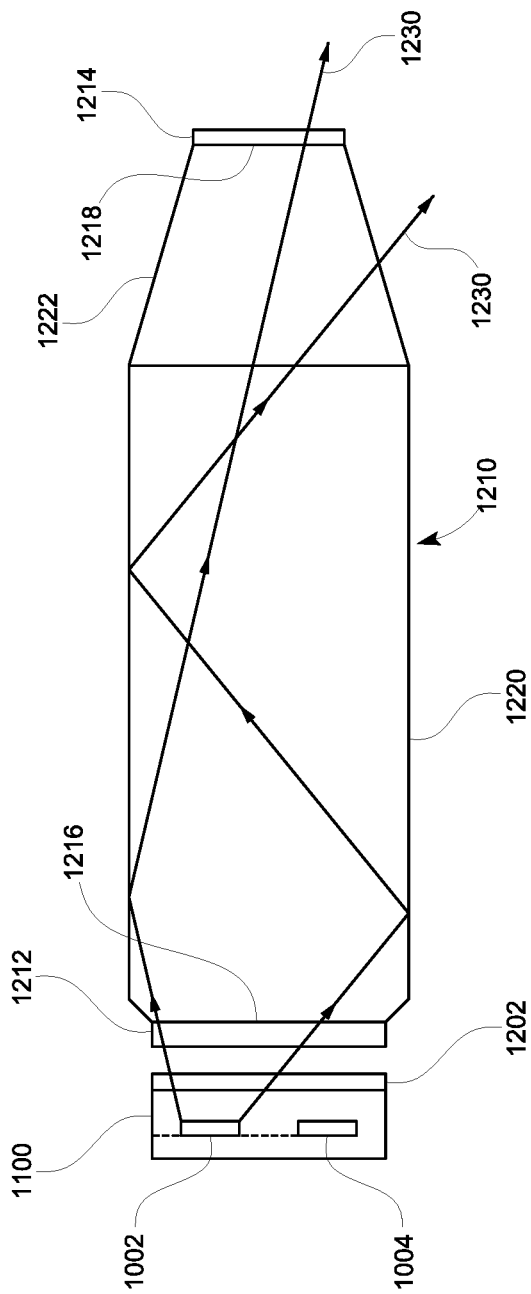
FIG. 12 is an exemplary diagram of UV light from the UV light source being directed into and through the optical plug, according to an embodiment.

FIG. 12 is an exemplary diagram of UV light from the UV light source being directed into and through the optical plug (not to scale), according to an embodiment. UV light source 1000 is shown with LEDs 1002 and 1004, and window 1202. Optical plug 1210 is shown with optional antireflective coatings 1212 and 1214 (not shown to scale). Antireflective coating 1212 is over base window 1216, and antireflective coating 1214 is over insertion window 1218. By way of non-limiting example, antireflective coatings 1212 and 1214 can be made from thin layers of materials such as Magnesium fluoride (MgF$_2$), fluoropolymers, and various other materials. Antireflective coatings 1212 and 1214 can be made of the same or different materials. Antireflective coating 1212 can help to ensure that a greater percentage of light from the LEDs enters through the base window 1216, and antireflective coating 1214 can help to ensure a greater percentage of light emerges out of the optical plug through the insertion window 1218. LED 1002 is shown emitting light rays 1230 through window 1202, and into the base window 1216 of the optical plug 1210. Optical plug 1210 can be designed to act as a light pipe, or light mixing rod, or light combiner. Optical plug 1210 can further be designed to act as a light homogenizer, or light homogenizing rod. Light 1230 can enter the optical plug 1210 through the base window 1216, and can then propagate through the optical plug via multiple internal reflections off the sidewalls of the optical plug. Additional light (not shown) from other LEDs such as 1002 can also enter the optical plug, and can propagate through the optical plug via multiple internal reflections off the sidewalls of the optical plug. In an embodiment, base end 1220 can cause light to reflect internally within the base end 1220, and insertion end 1222 can allow light to escape into the female Luer fitting and attached catheter. This internal reflection in the base end 1220 and escape from the insertion end 1222 can be controlled by the shape of the optical plug, the properties of the material used to make the optical plug, the grit and polish of the base end and the insertion end, or a combination of these factors. The reflection within the optical plug can mix the light from the different LEDs together so that polychromatic light, that can consist of different wavelengths of light, and can have each constituent wavelength have more uniform spatial distribution of intensity, can emerge from the optical plug through the insertion end 1222, the insertion window 1218, and through the antireflective coating 1214. The light from multiple sources can be reflected internally and mixed within the optical plug, and can emerge from the optical plug as a blended polychromatic light.

FIG. 13A shows light entering a female Luer fitting without an optical plug. As depicted, light 1304 from light source 1302 enters the female Luer fitting 210 at a narrow angle, and illuminates illumination area 1310, including the inner surface 1312 of the female Luer fitting 210 and the inner surface 1314 of the attached catheter. FIG. 13B shows light entering a female Luer fitting through the insertion end of an optical plug. Light is reflected internally and combined within the optical plug, and exits the insertion end of the optical plug at a broad range of angles. Light enters the female Luer fitting 210 from the optical plug 1340 at a broad range of angles, including light 1324 exiting from the front window of the optical plug and light 1326 exiting from the insertion sidewall of the optical plug. The light 1324 exiting from the front window of the optical plug has been reflected internally and redirected, and illuminates illumination area 1310 with a broad range of illumination angles, including the inner surface 1312 of the female Luer fitting 210 and the inner surface 1314 of the attached catheter. Because the light of FIG. 13A strikes illumination area 1310 at a narrow angle, the inner surface 1312 of the Luer fitting 210 is illuminated with a decreased intensity as compared with FIG. 13B. In FIG. 13B, light that is reflected internally within the optical plug 1340 exits from the insertion end 1342 at a much broader range of angles. This broader range of angles allows a greater light intensity to strike the inner surface 1312 of the Luer fitting 210 as compared to FIG. 13A.

Figure 14:
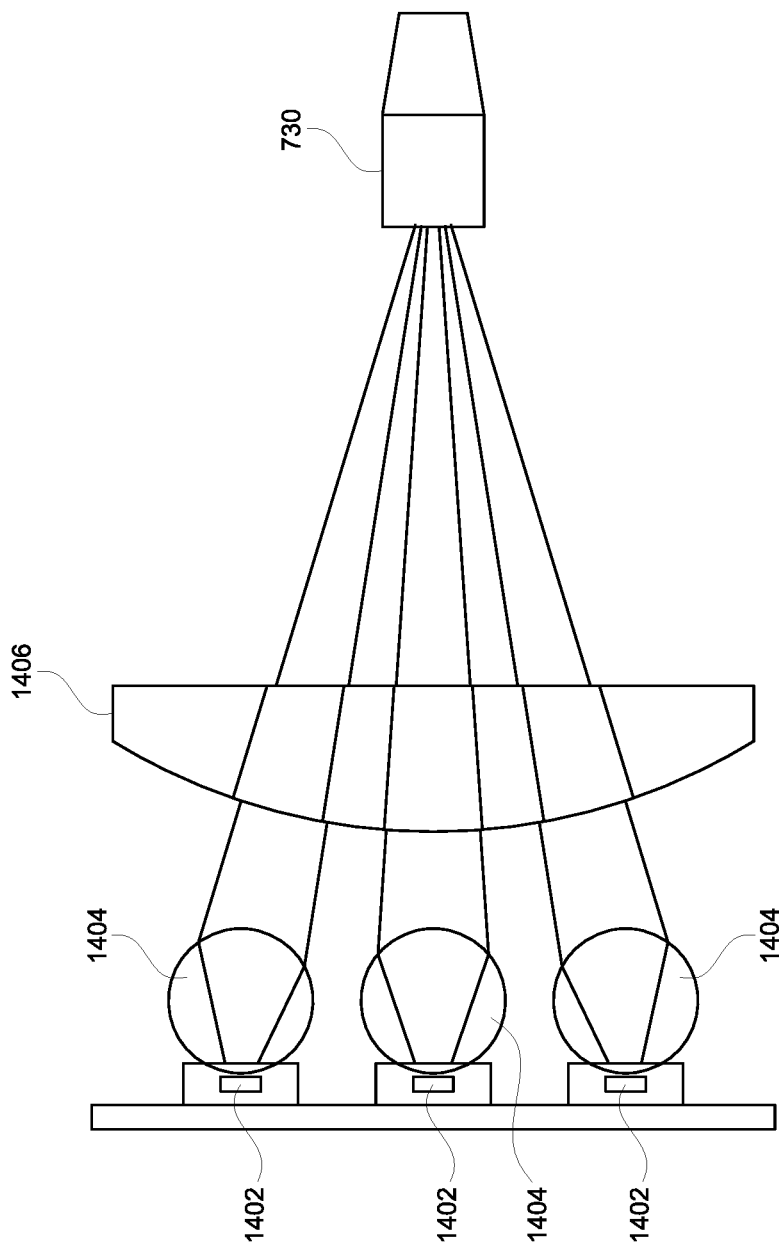
FIG. 14 shows a system of lenses for focusing UV light radiation, according to an embodiment.

FIG. 14 shows a system of lenses for focusing UV light radiation, according to an embodiment. The system of lenses for UV light radiation can be a component in the UV light unit 702. Light sources 1402, such as LEDs, can provide light in a range from approximately 180 nm to 700 nm, which can include light outside of the UV range. In some embodiments, light sources 1402 can include either UV-C sources, UV-A sources, or a combination of both. Spherical ball lenses 1404 can direct the light from a UV light source towards a focusing lens 1406. The focusing lens 1406 can direct the light out of the UV light unit and focus the light at the optical plug 730.

Figure 15:
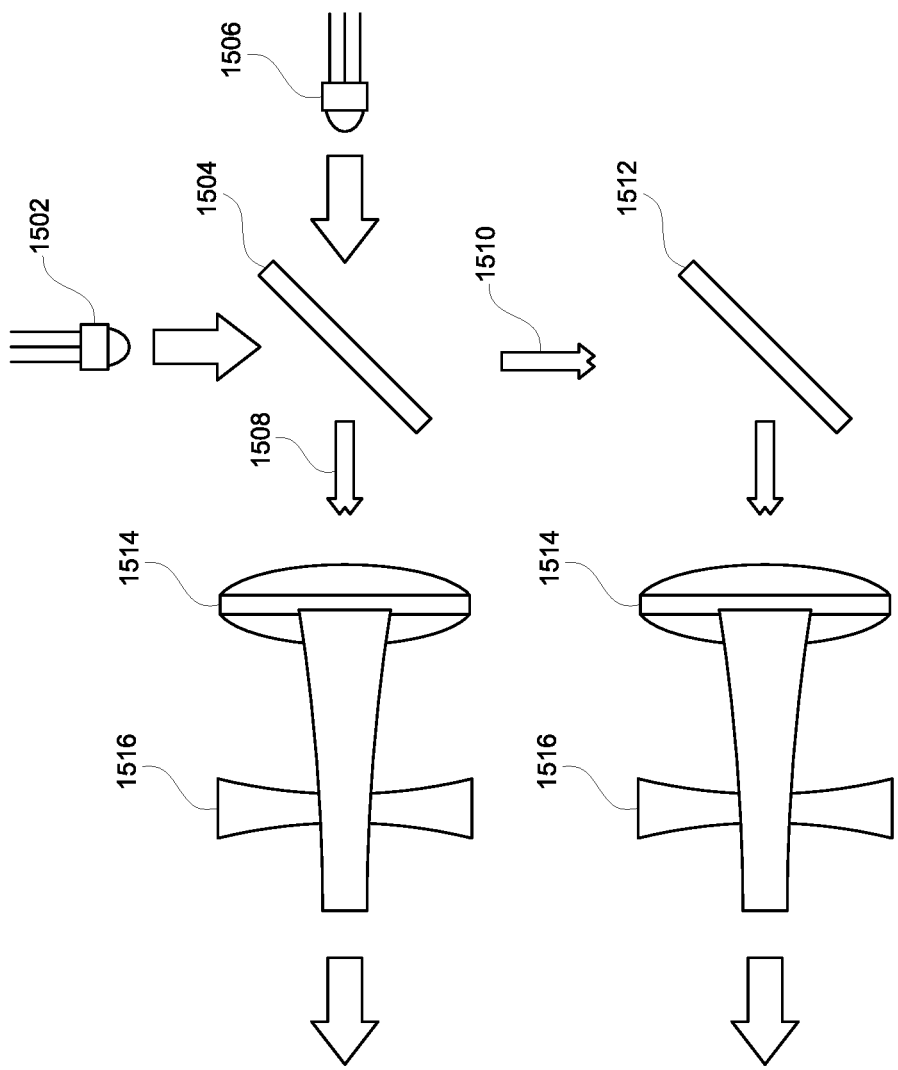
FIG. 15 shows a system for beam splitting and combining, according to an embodiment.

FIG. 15 shows a system for beam splitting and combining, according to an embodiment. A UV-C light source 1502, such as an LED, can project UV-C light onto a 50:50 UV fused silica quartz beamsplitter 1504. A UV-A light source 1506, such as an LED, can project UV-A light onto the 50:50 UV fused silica quartz beamsplitter 1504. The beamsplitter 1504 can produce two mixed wavelength beams 1508 and 1510 of approximately equal power. Beam 1510 can then be reflected off a mirror 1512. Each of these beams can then be passed through a dual lens beam shaping system. The first lens 1514 is a positive lens that can focus the beams 1508 and 1510. The second lens 1516 can then reshape the beams for projection through an optical plug 730 and into a catheter. This dual-lens combination of first a converging lens and then a diverging lens can reduce the beam diameter so that it matches the inlet diameter of the female Luer fitting. This system results in two separate beams of combined UV-C and UV-A light. This system can be used, for example, to irradiate a dual-port type hemodialysis catheter, as both ports can be treated simultaneously. Other optics designs are specifically contemplated, such as a knife-edge right-angle prism that could be used to combine the UV-A and UV-C light beams instead of a planar beam splitter.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, a UV LED or LEDs can be located outside of the sterilizer, and a fiber optic cable or other light guide/pipe can carry the UV light into the sterilizer. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Accordingly, this description is meant to be taken only by way of example, and not to otherwise limit the scope of this invention.

What is claimed is:

1. A sterilizer for sterilizing a female Luer fitting comprising:
   an optical plug comprising:
      a base end defining a base sidewall, the base sidewall having a first surface finish configured to enable internal reflection of incident light rays,
      a base window disposed at an end of the base end,
      an insertion end defining an insertion sidewall having a tapered frustoconical profile, the insertion sidewall having a second surface finish configured to enable diffusion of incident light rays, the second surface finish being distinct from the first surface finish, and
      a front window disposed at an end of the insertion end, wherein the insertion end is adapted to be inserted into the female Luer fitting with a first portion of insertion sidewall configured to mate with a corresponding tapered inner wall of the female Luer fitting such that the insertion end terminates within the female Luer fitting and the front window is disposed within the female Luer fitting;
   a sterilizer body comprising:
      a catheter harness adapted to enshroud a catheter tube and align the catheter tube in a straight line along an optical axis, and
      a female Luer fitting harness adapted to enshroud a female Luer fitting and a portion of the insertion sidewall and align the female Luer fitting along the optical axis; and
   at least one UV light source disposed at a distance from the base window and configured to emit UV light along the optical axis such that the UV light propagates through the base window, through the base end by internal reflection, and out of the insertion sidewall of the tapered frustoconical insertion end and front window of the optical plug, thereby irradiating the inner surfaces of the female Luer fitting and the inside of the catheter tube.

2. The sterilizer of claim 1, wherein the at least one UV light source is a UV-C light source.

3. The sterilizer of claim 2, wherein the UV-C light source provides light in a range of approximately 200 nm to 280 nm.

4. The sterilizer of claim 1, wherein the at least one UV light source is a UV-C light source and a UV-A light source.

5. The sterilizer of claim 4, wherein the UV-C light source provides light in a range of approximately 200 nm to 280 nm, and the UV-A light source provides light in a range of approximately 315 nm to 400 nm.

6. The sterilizer of claim 1, wherein the sterilizer also comprises a means of controlling or adjusting the light output or duty cycle of the at least one light source.

7. The sterilizer of claim 1, wherein the sterilizer body defines a sterilization chamber, with sterilization occurring within the sterilization chamber.

8. The sterilizer of claim 1, wherein the optical plug is a mixing rod.

9. The sterilizer of claim 1, wherein the optical plug is a light homogenizer.

10. The sterilizer of claim 1, wherein the catheter harness enshrouds at least 6 cm of the catheter tube.

11. The sterilizer of claim 1, wherein the catheter harness and female Luer fitting harness are a two-piece clamshell.

12. The sterilizer of claim 1, further comprising a user interface for controlling the duty cycle or pulse frequency of the light.

13. The sterilizer of claim 1, wherein the sterilizer body has an outer shell that comprises the catheter harness and the female Luer fitting harness, and wherein the outer shell fully encases the female Luer fitting and encases a portion of the catheter tube, the outer shell holding the optical plug within the female Luer fitting and sterilizing the catheter tube and the female Luer fitting.

14. The sterilizer of claim 1, wherein the catheter harness is adapted to encase at least 6 cm of the catheter tube and maintain the at least 6 cm of the catheter tube in a straight line extending outward from the UV light source.

15. The sterilizer of claim 1, wherein the insertion end defines a second portion configured to remain outside of the female Luer fitting.

16. The sterilizer of claim 1, wherein the first portion of the insertion sidewall comprises at least half of the insertion sidewall.

17. A sterilizer for sterilizing a female Luer fitting comprising:
   an optical plug comprising:
      a base end defining a base sidewall, the base sidewall having a first surface finish configured to enable internal reflection of incident light rays,
      a base window disposed at an end of the base end,
      an intermediate bevel,
      an insertion end defining an insertion sidewall having a tapered frustoconical profile, the insertion sidewall having a second surface finish configured to enable diffusion of incident light rays, the second surface finish being distinct from the first surface finish, and
      a front window disposed at an end of the insertion end having the second surface finish, wherein the insertion end is adapted to be inserted into the female Luer fitting with a first portion of insertion sidewall configured to mate with a corresponding tapered inner wall of the female Luer fitting such that the insertion end terminates within the female Luer fitting and the front window is disposed within the female Luer fitting;
   a sterilizer body comprising:
      a catheter harness adapted to enshroud a catheter tube and align the catheter tube in a straight line along an optical axis, and a female Luer fitting harness adapted to enshroud a female Luer fitting and a portion of the insertion sidewall and align the female Luer fitting along the optical axis; and at least one UV light source disposed at a distance from the base window and configured to emit UV light along the optical axis such that the UV light propagates through the base window, through the base end by internal reflection, and out of the insertion sidewall of the tapered frustoconical insertion end and front window of the optical plug, thereby irradiating the inner surfaces of the female Luer fitting and the inside of the catheter tube.

* * * * *